(12) United States Patent
Sutton et al.

(10) Patent No.: US 8,882,764 B2
(45) Date of Patent: *Nov. 11, 2014

(54) THERMAL DENERVATION DEVICES

(71) Applicant: Relievant Medsystems, Inc., Redwood City, CA (US)

(72) Inventors: Jeffrey K. Sutton, Medway, MA (US); Thomas Ryan, Austin, TX (US); Samit Patel, San Francisco, CA (US); Richard Pellegrino, Ashburn, VA (US)

(73) Assignee: Relievant Medsystems, Inc., Redwood City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/655,683

(22) Filed: Oct. 19, 2012

(65) Prior Publication Data

US 2013/0103022 A1 Apr. 25, 2013

Related U.S. Application Data

(63) Continuation of application No. 12/643,997, filed on Dec. 21, 2009, now abandoned, which is a continuation of application No. 11/745,446, filed on May 7, 2007, now abandoned, which is a continuation of application No. 10/401,854, filed on Mar. 28, 2003, now Pat. No. 7,258,690.

(51) Int. Cl.
*A61B 18/12* (2006.01)
*A61B 18/14* (2006.01)
*A61B 18/18* (2006.01)
*A61B 18/00* (2006.01)

(52) U.S. Cl.
CPC ........... *A61B 18/148* (2013.01); *A61B 18/1477* (2013.01); *A61B 2018/0044* (2013.01); *A61B 18/18* (2013.01); *A61B 2018/00791* (2013.01)
USPC .................. 606/41; 606/42; 606/43; 606/44; 606/45; 606/47; 606/48; 606/49; 606/50; 606/51; 606/52; 607/96; 607/98; 607/99; 607/100; 607/101

(58) Field of Classification Search
USPC ........................................................ 606/41
See application file for complete search history.

(56) References Cited

U.S. PATENT DOCUMENTS

| | | | |
|---|---|---|---|
| 3,845,771 | A | 11/1974 | Vise |
| 3,920,021 | A | 11/1975 | Hiltebrandt |

(Continued)

FOREIGN PATENT DOCUMENTS

| | | |
|---|---|---|
| EP | 0040658 | 12/1981 |
| EP | 0584959 | 3/1994 |

(Continued)

OTHER PUBLICATIONS

The AVAmax System—Cardinal Health Special Procedures, Lit. No. 25P0459-01—www.cardinal.com (2007).

(Continued)

*Primary Examiner* — Aaron Roane
(74) *Attorney, Agent, or Firm* — Knobbe, Martens, Olson & Bear LLP

(57) ABSTRACT

A method and apparatus for treating an intraosseous nerve. The method includes positioning a hollow shaft through the cortical shell of a vertebral body and into a cancellous bone region of the vertebral body. The hollow shaft includes an annular wall having a longitudinal bore therein, a proximal portion and a distal portion, and a first window extending transversely through the annular wall. An electrosurgical probe is advanced within the longitudinal bore from the proximal portion toward the distal portion. The electrosurgical probe includes a first treatment element at a distal end of the probe, wherein the first treatment element being in electrical connection with a power supply. The first treatment element is slidably disposed within the longitudinal bore so that the first treatment element is advanced radially outward from the window and shaft to affect treatment of the intraosseous nerve within the cancellous bone region.

8 Claims, 13 Drawing Sheets

(56) References Cited

U.S. PATENT DOCUMENTS

| | | |
|---|---|---|
| 4,044,774 A | 8/1977 | Corbin et al. |
| 4,116,198 A | 9/1978 | Roos |
| 4,312,364 A | 1/1982 | Convert et al. |
| 4,448,198 A | 5/1984 | Turner |
| 4,573,448 A | 3/1986 | Kambin |
| 4,657,017 A | 4/1987 | Sorochenko |
| 4,679,561 A | 7/1987 | Doss |
| 4,754,757 A | 7/1988 | Feucht |
| 4,907,589 A | 3/1990 | Cosman |
| 4,950,267 A | 8/1990 | Ishihara et al. |
| 4,959,063 A | 9/1990 | Kojima |
| 4,963,142 A | 10/1990 | Loertscher |
| 4,966,144 A | 10/1990 | Rochkind et al. |
| 5,061,266 A | 10/1991 | Hakky |
| 5,080,660 A | 1/1992 | Buelna |
| 5,084,043 A | 1/1992 | Hertzmann et al. |
| 5,098,431 A | 3/1992 | Rydell |
| 5,106,376 A | 4/1992 | Mononen et al. |
| 5,108,404 A | 4/1992 | Scholten et al. |
| 5,161,533 A | 11/1992 | Prass et al. |
| 5,190,546 A | 3/1993 | Jervis |
| 5,201,729 A | 4/1993 | Hertzmann et al. |
| 5,209,748 A | 5/1993 | Daikuzono |
| 5,222,953 A | 6/1993 | Dowlatshahi |
| 5,242,439 A | 9/1993 | Larsen et al. |
| 5,273,026 A | 12/1993 | Wilk |
| 5,281,213 A | 1/1994 | Milder et al. |
| 5,295,484 A | 3/1994 | Marcus et al. |
| 5,320,617 A | 6/1994 | Leach |
| 5,350,377 A | 9/1994 | Winston et al. |
| 5,366,443 A | 11/1994 | Eggers et al. |
| 5,368,031 A | 11/1994 | Cline et al. |
| 5,374,265 A | 12/1994 | Sand |
| 5,391,197 A | 2/1995 | Burdette et al. |
| 5,419,767 A | 5/1995 | Eggers et al. |
| 5,433,739 A | 7/1995 | Sluijter et al. |
| 5,437,661 A | 8/1995 | Rieser |
| 5,441,499 A | 8/1995 | Fritzsch |
| 5,443,463 A | 8/1995 | Stern et al. |
| 5,458,596 A | 10/1995 | Lax et al. |
| 5,458,597 A | 10/1995 | Edwards et al. |
| 5,472,441 A | 12/1995 | Edwards et al. |
| 5,484,432 A | 1/1996 | Sand |
| 5,486,170 A | 1/1996 | Winston et al. |
| 5,514,130 A | 5/1996 | Baker |
| 5,540,684 A | 7/1996 | Hassler, Jr. |
| 5,569,242 A | 10/1996 | Lax et al. |
| 5,571,147 A | 11/1996 | Sluijter et al. |
| 5,620,479 A | 4/1997 | Diederich |
| 5,630,426 A | 5/1997 | Shmulewitz et al. |
| 5,630,837 A | 5/1997 | Crowley |
| 5,643,319 A | 7/1997 | Green et al. |
| 5,647,871 A | 7/1997 | Levine et al. |
| 5,672,173 A | 9/1997 | Gough et al. |
| 5,681,282 A | 10/1997 | Eggers et al. |
| 5,683,366 A | 11/1997 | Eggers et al. |
| 5,693,052 A | 12/1997 | Weaver |
| 5,697,281 A | 12/1997 | Eggers et al. |
| 5,697,536 A | 12/1997 | Eggers et al. |
| 5,697,882 A | 12/1997 | Eggers et al. |
| 5,697,909 A | 12/1997 | Eggers et al. |
| 5,697,927 A | 12/1997 | Imran et al. |
| 5,700,262 A | 12/1997 | Acosta et al. |
| 5,720,287 A | 2/1998 | Chapelon et al. |
| 5,725,494 A | 3/1998 | Brisken |
| 5,728,062 A | 3/1998 | Brisken |
| 5,733,280 A | 3/1998 | Avitall |
| 5,733,315 A | 3/1998 | Burdette et al. |
| 5,735,811 A | 4/1998 | Brisken |
| 5,735,847 A | 4/1998 | Gough et al. |
| 5,738,680 A | 4/1998 | Mueller et al. |
| 5,743,904 A | 4/1998 | Edwards |
| 5,746,737 A | 5/1998 | Saadat |
| 5,752,969 A | 5/1998 | Cunci et al. |
| 5,762,066 A | 6/1998 | Law et al. |
| 5,762,616 A | 6/1998 | Talish |
| 5,766,153 A | 6/1998 | Eggers et al. |
| 5,776,092 A | 7/1998 | Farin et al. |
| 5,785,705 A | 7/1998 | Baker |
| 5,800,378 A | 9/1998 | Edwards et al. |
| 5,807,392 A | 9/1998 | Eggers |
| 5,810,764 A | 9/1998 | Eggers et al. |
| 5,817,021 A | 10/1998 | Reichenberger |
| 5,843,019 A | 12/1998 | Eggers et al. |
| 5,843,021 A | 12/1998 | Edwards et al. |
| 5,846,218 A | 12/1998 | Brisken et al. |
| 5,849,011 A | 12/1998 | Jones et al. |
| 5,855,576 A | 1/1999 | LeVeen et al. |
| 5,860,951 A | 1/1999 | Eggers et al. |
| 5,865,788 A | 2/1999 | Edwards et al. |
| 5,868,740 A | 2/1999 | LeVeen et al. |
| 5,871,469 A | 2/1999 | Eggers et al. |
| 5,871,470 A | 2/1999 | McWha |
| 5,871,481 A | 2/1999 | Kannenberg et al. |
| 5,873,855 A | 2/1999 | Eggers et al. |
| 5,873,877 A | 2/1999 | McGaffigan et al. |
| 5,888,198 A | 3/1999 | Eggers et al. |
| 5,891,095 A | 4/1999 | Eggers et al. |
| 5,895,370 A | 4/1999 | Edwards et al. |
| 5,902,272 A | 5/1999 | Eggers et al. |
| 5,904,681 A | 5/1999 | West, Jr. |
| 5,931,805 A | 8/1999 | Brisken |
| 5,935,123 A | 8/1999 | Edwards et al. |
| 5,941,722 A | 8/1999 | Chen |
| 5,941,876 A | 8/1999 | Nardella et al. |
| 5,944,715 A | 8/1999 | Goble et al. |
| 5,948,007 A | 9/1999 | Starkebaum et al. |
| 5,948,008 A | 9/1999 | Daikuzono |
| 5,954,716 A | 9/1999 | Sharkey et al. |
| 5,964,727 A | 10/1999 | Edwards et al. |
| 5,983,141 A | 11/1999 | Sluijter et al. |
| 5,997,497 A | 12/1999 | Nita et al. |
| 6,001,095 A | 12/1999 | de la Rama et al. |
| 6,007,533 A | 12/1999 | Casscells et al. |
| 6,007,570 A | 12/1999 | Sharkey et al. |
| 6,012,457 A | 1/2000 | Lesh |
| 6,016,452 A | 1/2000 | Kasevich |
| 6,017,356 A | 1/2000 | Frederick et al. |
| 6,022,334 A | 2/2000 | Edwards et al. |
| 6,024,733 A | 2/2000 | Eggers et al. |
| 6,024,740 A | 2/2000 | Lesh et al. |
| 6,030,402 A | 2/2000 | Thompson et al. |
| 6,032,674 A | 3/2000 | Eggers et al. |
| 6,035,238 A | 3/2000 | Ingle et al. |
| 6,045,532 A | 4/2000 | Eggers et al. |
| 6,050,995 A | 4/2000 | Durgin |
| 6,053,172 A | 4/2000 | Hovda et al. |
| 6,053,909 A | 4/2000 | Shadduck |
| 6,063,079 A | 5/2000 | Hovda et al. |
| 6,066,134 A | 5/2000 | Eggers et al. |
| 6,073,051 A | 6/2000 | Sharkey et al. |
| 6,086,585 A | 7/2000 | Hovda et al. |
| 6,090,105 A | 7/2000 | Zepeda et al. |
| 6,095,149 A | 8/2000 | Sharkey et al. |
| 6,099,514 A | 8/2000 | Sharkey et al. |
| 6,102,046 A | 8/2000 | Weinstein et al. |
| 6,104,957 A | 8/2000 | Alo et al. |
| 6,105,581 A | 8/2000 | Eggers et al. |
| 6,109,268 A | 8/2000 | Thaliyal et al. |
| 6,113,597 A | 9/2000 | Eggers et al. |
| 6,117,101 A | 9/2000 | Diederich et al. |
| 6,117,109 A | 9/2000 | Eggers et al. |
| 6,117,128 A | 9/2000 | Gregory |
| 6,120,467 A | 9/2000 | Schallhorn |
| 6,122,549 A | 9/2000 | Sharkey et al. |
| 6,139,545 A | 10/2000 | Utley et al. |
| 6,142,992 A | 11/2000 | Cheng et al. |
| 6,143,019 A | 11/2000 | Motamedi et al. |
| 6,146,380 A | 11/2000 | Racz et al. |
| 6,149,620 A | 11/2000 | Baker et al. |
| 6,159,194 A | 12/2000 | Eggers et al. |
| 6,159,208 A | 12/2000 | Hovda et al. |
| 6,161,048 A | 12/2000 | Sluijter et al. |
| 6,164,283 A | 12/2000 | Lesh |

(56) References Cited

U.S. PATENT DOCUMENTS

| | | | |
|---|---|---|---|
| 6,165,172 A | 12/2000 | Farley et al. |
| 6,168,593 B1 | 1/2001 | Sharkey et al. |
| 6,176,857 B1 | 1/2001 | Ashley |
| 6,179,824 B1 | 1/2001 | Eggers et al. |
| 6,179,836 B1 | 1/2001 | Eggers et al. |
| 6,183,469 B1 | 2/2001 | Thaliyal et al. |
| 6,190,381 B1 | 2/2001 | Olsen et al. |
| 6,190,383 B1 | 2/2001 | Schmaltz et al. |
| 6,193,715 B1 | 2/2001 | Wrublewski et al. |
| 6,203,542 B1 | 3/2001 | Ellsberry et al. |
| 6,210,393 B1 | 4/2001 | Brisken |
| 6,210,402 B1 | 4/2001 | Olsen et al. |
| 6,210,415 B1 | 4/2001 | Bester |
| 6,221,038 B1 | 4/2001 | Brisken |
| 6,224,592 B1 | 5/2001 | Eggers et al. |
| 6,228,046 B1 | 5/2001 | Brisken |
| 6,228,078 B1 | 5/2001 | Eggers et al. |
| 6,228,082 B1 | 5/2001 | Baker et al. |
| 6,231,571 B1 | 5/2001 | Ellman et al. |
| 6,231,615 B1 | 5/2001 | Preissman |
| 6,235,020 B1 | 5/2001 | Cheng et al. |
| 6,235,024 B1 | 5/2001 | Tu |
| 6,238,391 B1 | 5/2001 | Olsen et al. |
| 6,241,665 B1 | 6/2001 | Negus et al. |
| 6,241,725 B1 | 6/2001 | Cosman |
| 6,245,064 B1 | 6/2001 | Lesh et al. |
| 6,246,912 B1 | 6/2001 | Sluijter et al. |
| 6,254,553 B1 | 7/2001 | Lidgren et al. |
| 6,254,599 B1 | 7/2001 | Lesh et al. |
| 6,254,600 B1 | 7/2001 | Willink et al. |
| 6,258,086 B1 | 7/2001 | Ashley et al. |
| 6,259,952 B1 | 7/2001 | Sluijter |
| 6,261,311 B1 | 7/2001 | Sharkey et al. |
| 6,264,650 B1 | 7/2001 | Hovda et al. |
| 6,264,651 B1 | 7/2001 | Underwood et al. |
| 6,264,652 B1 | 7/2001 | Eggers et al. |
| 6,264,659 B1 | 7/2001 | Ross et al. |
| 6,267,770 B1 | 7/2001 | Truwit |
| 6,277,112 B1 | 8/2001 | Underwood et al. |
| 6,277,122 B1 | 8/2001 | McGahan et al. |
| 6,280,441 B1 | 8/2001 | Ryan |
| 6,283,961 B1 | 9/2001 | Underwood et al. |
| 6,287,114 B1 | 9/2001 | Meller et al. |
| 6,287,272 B1 | 9/2001 | Brisken et al. |
| 6,287,304 B1 | 9/2001 | Eggers et al. |
| 6,290,715 B1 | 9/2001 | Sharkey et al. |
| 6,296,619 B1 | 10/2001 | Brisken et al. |
| 6,296,636 B1 | 10/2001 | Cheng et al. |
| 6,296,638 B1 | 10/2001 | Davison et al. |
| 6,305,378 B1 | 10/2001 | Lesh et al. |
| 6,309,387 B1 | 10/2001 | Eggers et al. |
| 6,309,420 B1 | 10/2001 | Preissman |
| 6,312,408 B1 | 11/2001 | Eggers et al. |
| 6,312,426 B1 | 11/2001 | Goldberg et al. |
| 6,322,549 B1 | 11/2001 | Eggers et al. |
| 6,348,055 B1 | 2/2002 | Preissman |
| 6,355,032 B1 | 3/2002 | Hovda et al. |
| 6,363,937 B1 | 4/2002 | Hovda et al. |
| 6,379,351 B1 | 4/2002 | Thaliyal et al. |
| 6,383,190 B1 | 5/2002 | Preissman |
| 6,391,025 B1 | 5/2002 | Weinstein et al. |
| 6,416,507 B1 | 7/2002 | Eggers et al. |
| 6,416,508 B1 | 7/2002 | Eggers et al. |
| 6,423,059 B1 | 7/2002 | Hanson et al. |
| 6,432,103 B1 | 8/2002 | Ellsberry et al. |
| 6,436,060 B1 | 8/2002 | Talish |
| 6,451,013 B1 | 9/2002 | Bays et al. |
| 6,454,727 B1 | 9/2002 | Burbank et al. |
| 6,461,350 B1 | 10/2002 | Underwood et al. |
| 6,461,354 B1 | 10/2002 | Olsen et al. |
| 6,464,695 B2 | 10/2002 | Hovda et al. |
| 6,468,270 B1 | 10/2002 | Hovda et al. |
| 6,468,274 B1 | 10/2002 | Alleyne et al. |
| 6,478,793 B1 | 11/2002 | Cosman et al. |
| 6,482,201 B1 | 11/2002 | Olsen et al. |
| 6,500,173 B2 | 12/2002 | Underwood et al. |
| 6,527,759 B1 | 3/2003 | Tachibana et al. |
| 6,540,741 B1 | 4/2003 | Underwood et al. |
| 6,544,261 B2 | 4/2003 | Ellsberry et al. |
| 6,557,559 B1 | 5/2003 | Eggers et al. |
| 6,558,385 B1 | 5/2003 | McClurken et al. |
| 6,560,486 B1 | 5/2003 | Osorio et al. |
| 6,575,968 B1 | 6/2003 | Eggers et al. |
| 6,582,423 B1 | 6/2003 | Thaliyal et al. |
| 6,585,656 B2 | 7/2003 | Masters |
| 6,589,237 B2 | 7/2003 | Woloszko et al. |
| 6,595,990 B1 | 7/2003 | Weinstein et al. |
| 6,602,248 B1 | 8/2003 | Sharps et al. |
| 6,622,731 B2 | 9/2003 | Daniel et al. |
| 6,632,193 B1 | 10/2003 | Davison et al. |
| 6,632,220 B1 | 10/2003 | Eggers et al. |
| 6,659,106 B1 | 12/2003 | Hovda et al. |
| 6,699,242 B2 | 3/2004 | Heggeness |
| 6,726,684 B1 | 4/2004 | Woloszko et al. |
| 6,736,835 B2 | 5/2004 | Pellegrino et al. |
| 6,746,447 B2 | 6/2004 | Davison et al. |
| 6,749,604 B1 | 6/2004 | Eggers et al. |
| 6,758,846 B2 | 7/2004 | Goble et al. |
| 6,770,071 B2 | 8/2004 | Woloszko et al. |
| 6,772,012 B2 | 8/2004 | Ricart et al. |
| 6,773,431 B2 | 8/2004 | Eggers et al. |
| 6,827,716 B2 | 12/2004 | Ryan et al. |
| 6,832,996 B2 | 12/2004 | Woloszko et al. |
| 6,837,887 B2 | 1/2005 | Woloszko et al. |
| 6,837,888 B2 | 1/2005 | Ciarrocca et al. |
| 6,863,672 B2 | 3/2005 | Reiley et al. |
| 6,875,219 B2 | 4/2005 | Arramon et al. |
| 6,881,214 B2 | 4/2005 | Cosman et al. |
| 6,896,674 B1 | 5/2005 | Woloszko et al. |
| 6,907,884 B2 | 6/2005 | Pellegrino et al. |
| 6,915,806 B2 | 7/2005 | Pacek et al. |
| 6,922,579 B2 | 7/2005 | Taimisto et al. |
| 6,923,813 B2 | 8/2005 | Phillips et al. |
| 6,960,204 B2 | 11/2005 | Eggers et al. |
| 6,974,453 B2 | 12/2005 | Woloszko et al. |
| 7,048,743 B2 | 5/2006 | Miller et al. |
| 7,090,672 B2 | 8/2006 | Underwood et al. |
| 7,131,969 B1 | 11/2006 | Hovda et al. |
| 7,177,678 B1 | 2/2007 | Osorio et al. |
| 7,179,255 B2 | 2/2007 | Lettice et al. |
| 7,186,234 B2 | 3/2007 | Dahla et al. |
| 7,192,428 B2 | 3/2007 | Eggers et al. |
| 7,201,731 B1 | 4/2007 | Lundquist et al. |
| 7,201,750 B1 | 4/2007 | Eggers et al. |
| 7,211,055 B2 | 5/2007 | Diederich et al. |
| 7,217,268 B2 | 5/2007 | Eggers et al. |
| 7,258,690 B2 * | 8/2007 | Sutton et al. .................. 606/45 |
| 7,270,659 B2 | 9/2007 | Ricart et al. |
| 7,270,661 B2 | 9/2007 | Dahla et al. |
| 7,276,063 B2 | 10/2007 | Davison et al. |
| 7,318,823 B2 | 1/2008 | Sharps et al. |
| 7,326,203 B2 | 2/2008 | Papineau et al. |
| 7,331,957 B2 | 2/2008 | Woloszko et al. |
| RE40,156 E | 3/2008 | Sharps et al. |
| 7,346,391 B1 | 3/2008 | Osorio et al. |
| 7,386,350 B2 | 6/2008 | Vilims |
| 7,387,625 B2 | 6/2008 | Hovda et al. |
| 7,393,351 B2 | 7/2008 | Woloszko et al. |
| 7,422,585 B1 | 9/2008 | Eggers et al. |
| 7,429,262 B2 | 9/2008 | Woloszko et al. |
| 7,435,247 B2 | 10/2008 | Woloszko et al. |
| 7,442,191 B2 | 10/2008 | Hovda et al. |
| 7,468,059 B2 | 12/2008 | Eggers et al. |
| 7,480,533 B2 | 1/2009 | Cosman et al. |
| 7,502,652 B2 | 3/2009 | Gaunt et al. |
| 7,507,236 B2 | 3/2009 | Eggers et al. |
| 7,553,307 B2 | 6/2009 | Bleich et al. |
| 7,555,343 B2 | 6/2009 | Bleich |
| 7,645,277 B2 | 1/2010 | McClurken et al. |
| 7,738,968 B2 | 6/2010 | Bleich |
| 7,740,631 B2 | 6/2010 | Bleich et al. |
| 7,749,218 B2 | 7/2010 | Pellegrino et al. |
| 7,819,826 B2 | 10/2010 | Diederich et al. |
| 7,819,869 B2 | 10/2010 | Godara et al. |

(56) References Cited

U.S. PATENT DOCUMENTS

| | | |
|---|---|---|
| 7,824,398 B2 | 11/2010 | Woloszko et al. |
| 7,824,404 B2 | 11/2010 | Godara et al. |
| 7,857,813 B2 | 12/2010 | Schmitz et al. |
| 7,901,403 B2 | 3/2011 | Woloszko et al. |
| 7,909,827 B2 | 3/2011 | Reiley et al. |
| 7,917,222 B1 | 3/2011 | Osorio et al. |
| 7,918,849 B2 | 4/2011 | Bleich et al. |
| 7,945,331 B2 | 5/2011 | Vilims |
| 7,963,915 B2 | 6/2011 | Bleich |
| 8,066,702 B2 | 11/2011 | Rittman, III et al. |
| 8,083,736 B2 | 12/2011 | McClurken et al. |
| 8,100,896 B2 | 1/2012 | Podhajsky |
| 8,192,424 B2 | 6/2012 | Woloszko et al. |
| 8,192,435 B2 | 6/2012 | Bleich et al. |
| 8,265,747 B2 | 9/2012 | Rittman, III et al. |
| 8,282,628 B2 | 10/2012 | Paul et al. |
| 8,292,887 B2 | 10/2012 | Woloszko et al. |
| 8,323,279 B2 | 12/2012 | Dahla et al. |
| 8,355,791 B2 | 1/2013 | Moffitt |
| 8,361,067 B2 | 1/2013 | Pellegrino et al. |
| 8,414,509 B2 | 4/2013 | Diederich et al. |
| 8,414,571 B2 | 4/2013 | Pellegrino et al. |
| 8,419,730 B2 | 4/2013 | Pellegrino et al. |
| 8,419,731 B2 | 4/2013 | Pellegrino et al. |
| 8,425,507 B2 | 4/2013 | Pellegrino et al. |
| 8,535,309 B2 | 9/2013 | Pellegrino et al. |
| 8,613,744 B2 | 12/2013 | Pellegrino et al. |
| 8,623,014 B2 | 1/2014 | Pellegrino et al. |
| 8,628,528 B2 | 1/2014 | Pellegrino et al. |
| 2001/0001314 A1 | 5/2001 | Davison et al. |
| 2001/0001811 A1 | 5/2001 | Burney et al. |
| 2001/0020167 A1 | 9/2001 | Woloszko et al. |
| 2001/0023348 A1 | 9/2001 | Ashley et al. |
| 2001/0025176 A1 | 9/2001 | Ellsberry et al. |
| 2001/0025177 A1 | 9/2001 | Woloszko et al. |
| 2001/0029370 A1 | 10/2001 | Hodva et al. |
| 2001/0029373 A1 | 10/2001 | Baker et al. |
| 2001/0032001 A1 | 10/2001 | Ricart et al. |
| 2001/0047167 A1 | 11/2001 | Heggeness |
| 2001/0049522 A1 | 12/2001 | Eggers et al. |
| 2001/0051802 A1 | 12/2001 | Woloszko et al. |
| 2001/0056280 A1 | 12/2001 | Underwood et al. |
| 2002/0016600 A1 | 2/2002 | Cosman |
| 2002/0019626 A1 | 2/2002 | Sharkey et al. |
| 2002/0026186 A1 | 2/2002 | Woloszko et al. |
| 2002/0052600 A1 | 5/2002 | Davison et al. |
| 2002/0068930 A1 | 6/2002 | Tasto et al. |
| 2002/0095151 A1 | 7/2002 | Dahla et al. |
| 2002/0095152 A1 | 7/2002 | Ciarrocca et al. |
| 2002/0099366 A1 | 7/2002 | Dahla et al. |
| 2002/0120259 A1 | 8/2002 | Lettice et al. |
| 2002/0147444 A1 | 10/2002 | Shah et al. |
| 2002/0151885 A1 | 10/2002 | Underwood et al. |
| 2002/0188284 A1 | 12/2002 | To et al. |
| 2002/0193789 A1 | 12/2002 | Underwood et al. |
| 2003/0009164 A1 | 1/2003 | Woloszko et al. |
| 2003/0014047 A1 | 1/2003 | Woloszko et al. |
| 2003/0028189 A1 | 2/2003 | Woloszko et al. |
| 2003/0040742 A1 | 2/2003 | Underwood et al. |
| 2003/0055418 A1 | 3/2003 | Tasto et al. |
| 2003/0084907 A1 | 5/2003 | Pacek et al. |
| 2003/0097126 A1 | 5/2003 | Woloszko et al. |
| 2003/0097129 A1 | 5/2003 | Davison et al. |
| 2003/0130655 A1 | 7/2003 | Woloszko et al. |
| 2003/0158545 A1 | 8/2003 | Hovda et al. |
| 2003/0181963 A1 | 9/2003 | Pellegrino et al. |
| 2003/0208194 A1 | 11/2003 | Hovda et al. |
| 2003/0216725 A1 | 11/2003 | Woloszko et al. |
| 2003/0216726 A1 | 11/2003 | Eggers et al. |
| 2004/0006339 A1 | 1/2004 | Underwood et al. |
| 2004/0024399 A1 | 2/2004 | Sharps et al. |
| 2004/0054366 A1 | 3/2004 | Davison et al. |
| 2004/0087937 A1 | 5/2004 | Eggers et al. |
| 2004/0133124 A1 | 7/2004 | Bates et al. |
| 2004/0162559 A1 | 8/2004 | Arramon |
| 2004/0193151 A1 | 9/2004 | To et al. |
| 2004/0220577 A1 | 11/2004 | Cragg et al. |
| 2004/0230190 A1 | 11/2004 | Dahla et al. |
| 2005/0004634 A1 | 1/2005 | Ricart et al. |
| 2005/0010203 A1 | 1/2005 | Edwards et al. |
| 2005/0010205 A1 | 1/2005 | Hovda et al. |
| 2005/0182417 A1 | 8/2005 | Pagano |
| 2005/0192564 A1 | 9/2005 | Cosman et al. |
| 2005/0209659 A1 | 9/2005 | Pellegrino et al. |
| 2005/0283148 A1 | 12/2005 | Janssen et al. |
| 2006/0004369 A1 | 1/2006 | Patel et al. |
| 2006/0064101 A1 | 3/2006 | Arramon |
| 2006/0095026 A1 | 5/2006 | Ricart et al. |
| 2006/0095028 A1 | 5/2006 | Bleich |
| 2006/0122458 A1 | 6/2006 | Bleich |
| 2006/0129101 A1 | 6/2006 | McGuckin |
| 2006/0178670 A1 | 8/2006 | Woloszko et al. |
| 2006/0229625 A1 | 10/2006 | Truckai et al. |
| 2006/0253117 A1 | 11/2006 | Hovda et al. |
| 2006/0264957 A1 | 11/2006 | Cragg et al. |
| 2006/0276749 A1 | 12/2006 | Selmon et al. |
| 2007/0118142 A1 | 5/2007 | Krueger et al. |
| 2007/0129715 A1 | 6/2007 | Eggers et al. |
| 2007/0149966 A1 | 6/2007 | Dahla et al. |
| 2007/0179497 A1 | 8/2007 | Eggers et al. |
| 2007/0260237 A1 | 11/2007 | Sutton et al. |
| 2008/0004621 A1 | 1/2008 | Dahla et al. |
| 2008/0004675 A1 | 1/2008 | King et al. |
| 2008/0009847 A1 | 1/2008 | Ricart et al. |
| 2008/0021447 A1 | 1/2008 | Davison et al. |
| 2008/0021463 A1 | 1/2008 | Georgy |
| 2008/0058707 A1 | 3/2008 | Ashley et al. |
| 2008/0114364 A1 | 5/2008 | Goldin et al. |
| 2008/0119844 A1 | 5/2008 | Woloszko et al. |
| 2008/0119846 A1 | 5/2008 | Rioux |
| 2008/0132890 A1 | 6/2008 | Woloszko et al. |
| 2008/0161804 A1 | 7/2008 | Rioux et al. |
| 2008/0275458 A1 | 11/2008 | Bleich et al. |
| 2009/0030308 A1 | 1/2009 | Bradford et al. |
| 2009/0069807 A1 | 3/2009 | Eggers et al. |
| 2009/0105775 A1 | 4/2009 | Mitchell et al. |
| 2009/0118731 A1 | 5/2009 | Young et al. |
| 2009/0131867 A1 | 5/2009 | Liu et al. |
| 2009/0131886 A1 | 5/2009 | Liu et al. |
| 2009/0222053 A1 | 9/2009 | Gaunt et al. |
| 2009/0312764 A1 | 12/2009 | Marino |
| 2010/0016929 A1 | 1/2010 | Prochazka |
| 2010/0023006 A1 | 1/2010 | Ellman |
| 2010/0082033 A1 | 4/2010 | Germain |
| 2010/0094269 A1 | 4/2010 | Pellegrino et al. |
| 2010/0114098 A1 | 5/2010 | Carl |
| 2010/0145424 A1 | 6/2010 | Podhajsky et al. |
| 2010/0185161 A1 | 7/2010 | Pellegrino et al. |
| 2010/0211076 A1 | 8/2010 | Germain et al. |
| 2010/0222777 A1 | 9/2010 | Sutton et al. |
| 2010/0298832 A1 | 11/2010 | Lau et al. |
| 2010/0324506 A1 | 12/2010 | Pellegrino et al. |
| 2011/0022133 A1 | 1/2011 | Diederich et al. |
| 2011/0034884 A9 | 2/2011 | Pellegrino et al. |
| 2011/0040362 A1 | 2/2011 | Godara et al. |
| 2011/0077628 A1 | 3/2011 | Hoey et al. |
| 2011/0087314 A1 | 4/2011 | Diederich et al. |
| 2011/0196361 A1 | 8/2011 | Vilims |
| 2011/0264098 A1 | 10/2011 | Cobbs |
| 2011/0276001 A1 | 11/2011 | Schultz et al. |
| 2011/0319765 A1 | 12/2011 | Gertner et al. |
| 2012/0029420 A1 | 2/2012 | Rittman, III et al. |
| 2012/0196251 A1 | 8/2012 | Taft et al. |
| 2012/0197344 A1 | 8/2012 | Taft et al. |
| 2012/0203219 A1 | 8/2012 | Evans et al. |
| 2012/0226273 A1 | 9/2012 | Nguyen et al. |
| 2012/0239050 A1 | 9/2012 | Linderman |
| 2012/0330180 A1 | 12/2012 | Pellegrino et al. |
| 2012/0330300 A1 | 12/2012 | Pellegrino et al. |
| 2012/0330301 A1 | 12/2012 | Pellegrino et al. |
| 2013/0006232 A1 | 1/2013 | Pellegrino et al. |
| 2013/0006233 A1 | 1/2013 | Pellegrino et al. |
| 2013/0012933 A1 | 1/2013 | Pellegrino et al. |
| 2013/0012935 A1 | 1/2013 | Pellegrino et al. |

(56) References Cited

U.S. PATENT DOCUMENTS

| | | | |
|---|---|---|---|
| 2013/0012936 A1 | 1/2013 | Pellegrino et al. | |
| 2013/0103022 A1 | 4/2013 | Pellegrino et al. | |
| 2013/0261507 A1 | 10/2013 | Diederich et al. | |
| 2013/0324994 A1 | 12/2013 | Pellegrino et al. | |
| 2013/0324996 A1 | 12/2013 | Pellegrino et al. | |
| 2013/0324997 A1 | 12/2013 | Pellegrino et al. | |
| 2014/0039500 A1 | 2/2014 | Pellegrino et al. | |

FOREIGN PATENT DOCUMENTS

| | | |
|---|---|---|
| EP | 0597463 | 5/1994 |
| EP | 1013228 | 6/2000 |
| EP | 1059067 | 12/2000 |
| EP | 1059087 | 12/2000 |
| JP | 6-47058 | 2/1994 |
| JP | 2001-037760 | 2/2001 |
| JP | 2002-531229 | 9/2002 |
| WO | WO 96/36289 | 11/1996 |
| WO | WO 98/27876 | 7/1998 |
| WO | WO 98/34550 | 8/1998 |
| WO | WO 99/19025 | 4/1999 |
| WO | WO 99/44519 | 9/1999 |
| WO | WO 99/48621 | 9/1999 |
| WO | WO 00/21448 | 4/2000 |
| WO | WO 00/33909 | 6/2000 |
| WO | WO 00/49978 | 8/2000 |
| WO | WO 00/56237 | 9/2000 |
| WO | WO 00/67648 | 11/2000 |
| WO | WO 00/67656 | 11/2000 |
| WO | WO 01/01877 | 1/2001 |
| WO | WO 01/26570 | 4/2001 |
| WO | WO 01/45579 | 6/2001 |
| WO | WO 01/57655 | 8/2001 |
| WO | WO 02/05699 | 1/2002 |
| WO | WO 02/28302 | 4/2002 |
| WO | WO 02/054941 | 7/2002 |
| WO | WO 02/067797 | 9/2002 |
| WO | WO 02/096304 | 12/2002 |
| WO | WO2007/031264 | 3/2007 |
| WO | WO 2008/008522 | 1/2008 |
| WO | WO 2008/121259 | 10/2008 |

OTHER PUBLICATIONS

Mary S. Sherman; The Nerves of Bone, The Journal of Bone and Joint Surgery, Apr. 1963, pp. 522-528, vol. 45-A, No. 3.

Michael H. Heggeness, et al., The Trabecular Anatomy of Thoracolumbar Vertebrae: Implications for Burst Fractures, Journal of Anatomy, 1997, pp. 309-312, vol. 191, Great Britain.

J.B. Martin, et al., Vertebroplasty: Clinical Experience and Follow-up Results, Bone, Aug. 1999, pp. 11S-15S, vol. 25, No. 2, Supplement.

H. Deramond, et al., Temperature Elevation Caused by Bone Cement Polymerization During Vertebroplasty, Bone, Aug. 1999, pp. 17S-21S, vol. 25, No. 2, Supplement.

D.E. Dupuy et al. Radiofrequency ablation of spinal tumors: Temperature distribution in the spinal canal AJR, vol. 175, pp. 1263-1266, Nov. 2000.

C.L. Tillotson et al. Controlled thermal injury of bone: Report of a percutaneous technique using radiofrequency electrode and generator. Investigative Radiology, Nov. 1989, pp. 888-892.

Cosman, E.R. et al. Theoretical Aspects of Radiofrequency Lesions in the Dorsal Root Entry Zone. Neurosurgery, vol. 1, No. 6, 1984, pp. 945-950.

S.N. Goldberg et al. Tissue ablation with radiofrequency: Effect of probe size, gauge, duration, and temperature on lesion volume, Acad. Radiol., vol. 2, pp. 399-404 (1995).

D.I. Rosenthal. Seminars in Musculoskeletal Radiology, vol. 1, No. 2, pp. 265-272 (1997).

L. Solbiati et al. Hepatic metastases: Percutaneous radio-frequency ablation with cooled-tip electrodes. Interventional Radiology, vol. 205, No. 2, pp. 367-373 (1997).

Massad, Malek M.D. et al.; Endoscopic Thoracic Sympathectomy: Evaluation of Pulsatile Laser, Non-Pulsatile Laser, and Radiofrequency-Generated Thermocoagulation; Lasers in Surgery and Medicine; 1991; pp. 18-25.

Kleinstueck, Frank S. et al.; Acute Biomechanical and Histological Effects of Intradiscal Electrothermal Therapy on Human Lumbar Discs; SPINE vol. 26, No. 20, pp. 2198-2207; 2001, Lippincott Williams & Wilkins, Inc.

Heggeness, Michael H. et al. Discography Causes End Plate Deflection; SPINE vol. 18, No. 8, pp. 1050-1053, 1993, J.B. Lippincott Company.

Letcher, Frank S. et al.; The Effect of Radiofrequency Current and Heat on Peripheral Nerve Action Potential in the Cat; U.S. Naval Hospital, Philadelphia, PA (1968).

Houpt, Jonathan C. et al.; Experimental Study of Temperature Distributions and Thermal Transport During Radiofrequency Current Therapy of the Intervertebral Disc; SPINE vol. 21, No. 15, pp. 1808-1813, 1996, Lippincott-Raven Publishers.

Lundskog, Jan; Heat and Bone Tissue-/an experimental investigation of the thermal properties of bone tissue and threshold levels for thermal injury; Scandinavian Journal of Plastic and Reconstructive Surgery Supplemental 9, From the Laboratory of Experimental Biology, Department of anatomy, University of Gothenburg, Gothenburg, Sweden, Goteborg (1972).

Antonacci, M. Darryl et al.; Innervation of the Human Vertebral Body: A Histologic Study; Journal of Spinal Disorder, vol. 11, No. 6, pp. 526-531, 1998 Lippincott Williams & Wilkins, Philadelphia.

Arnoldi, Carl C.; Intraosseous Hypertension—A Possible Cause of Low Back Pain?; Clinical Orthopedics and Related Research, No. 115, Mar.-Apr. 1976.

Esses, Stephen I. et al.; Intraosseous Vertebral Body Pressures; SPINE vol. 17 No. 6 Supplement (1992).

Troussier, B. et al.; Percutaneous Intradiscal Radio-Frequency Thermocoagulation A Cadaveric Study; SPINE vol. 20, No. 15, pp. 1713-1718, 1995, Lippincott-Raven Publishers.

Choy, Daniel SS.J. et al.; Percutaneous Laser Disc Decompression, A New Therapeutic Modality; SPINE vol. 17, No. 8 (1992).

Shealy, C. Norman; Percutaneous radiofrequency denervation of spinal facets: Treatment for chronic back pain and sciatica; Journal of Neurosurgery/vol. 43/Oct. 1975.

Depuy, Damian E.; Radiofrequency Ablation: An Outpatient Percutaneous Treatment; Medicine and Health/Rhode Island vol. 82, No. 6, Jun. 1999.

Rashbaum, Ralph F.; Radiofrequency Facet Denervation A Treatment alternative in Refractory Low Back Pain with or without Leg Pain; Orthopedic Clinics of North America—vol. 14, No. 3, Jul. 1983.

Lehmann, Justus F. et al.; Selective Heating Effects of Ultrasound in Human Beings; Archives of Physical Medicine & Rehabilitation Jun. 1966.

Hanai, Kenji et al.; Simultaneous Measurement of Intraosseous and Cerebrospinal Fluid Pressures in the Lumbar Region; SPINE vol. 10, No. 1 (1985).

Bogduk, Nikolai, et al.; Technical Limitations to the efficacy of Radiofrequency Neurotomy for Spinal Pain; Neurosurgery vol. 20, No. 4 (1987).

Mehta, Mark et al.; The treatment of chronic back pain; Anaesthesia, 1979, vol. 34, pp. 768-775.

Deardorff, Dana L. et al.; Ultrasound applicators with internal cooling for interstitial thermal therapy; SPIE vol. 3594 (1999).

Diederich, Chris J. et al.; Ultrasound Catheters for Circumferential Cardiac Ablation; SPIE vol. 3594 (1999).

Diederich C J, et al. "IDTT Therapy in Cadaveric Lumbar Spine: Temperature and thermal dose distributions, Thermal Treatment of Tissue: Energy Delivery and Assessment," Thomas P. Ryan, Editor, Proceedings of SPIE vol. 4247:104-108 (2001).

Nau, William H., Ultrasound interstitial thermal therapy (USITT) in the prostate; SPIE vol. 3594 (1999).

The AVAmax System—Cardinal Health Special Procedures, Lit. No. 25P0459-01—www.cardinal.com (allegedly dated 2007).

Kopecky, Kenyon K. et al. "Side-Exiting Coaxial Needle for Aspiration Biopsy"—AJR—1996; 167, pp. 661-662.

(56) References Cited

OTHER PUBLICATIONS

A Novel Approach for Treating Chronic Lower Back Pain, Abstract for Presentation at North American Spine Society 26th Annual Meeting in Chicago, IL on Nov. 4, 2011.

Stanton, Terry, "Can Nerve Ablation Reduce Chronic Back Pain?" AAOS Now Jan. 2012.

Ryan et al., "Three-Dimensional Finite Element Simulations of Vertebral Body Thermal Treatment," Thermal Treatment of Tissue: Energy Delivery and Assessment III, edited by Thomas P. Ryan, Proceedings of SPIE, vol. 5698 (SPIE, Bellingham, WA, 2005) pp. 137-155.

Bergeron et al., "Fluoroscopic-guided radiofrequency ablation of the basivertebral nerve: application and analysis with multiple imaging modalities in an ovine model," Thermal Treatment of Tissue: Energy Delivery and Assessment III, edited by Thomas P. Ryan, Proceedings of SPIE, vol. 5698 (SPIE, Bellingham, WA, 2005) pp. 156-167.

Hoopes et al., "Radiofrequency Ablation of The Basivertebral Nerve as a Potential Treatment of Back Pain: Pathologic Assessment in an Ovine Model," Thermal Treatment of Tissue: Energy Delivery and Assessment III, edited by Thomas P. Ryan, Proceedings of SPIE, vol. 5698 (SPIE, Bellingham, WA, 2005) pp. 168-180.

FDA Response to 510(k) Submission by Relievant Medsystems, Inc. submitted on Sep. 27, 2007 (date stamped on Oct. 5, 2007) and associated documents.

* cited by examiner

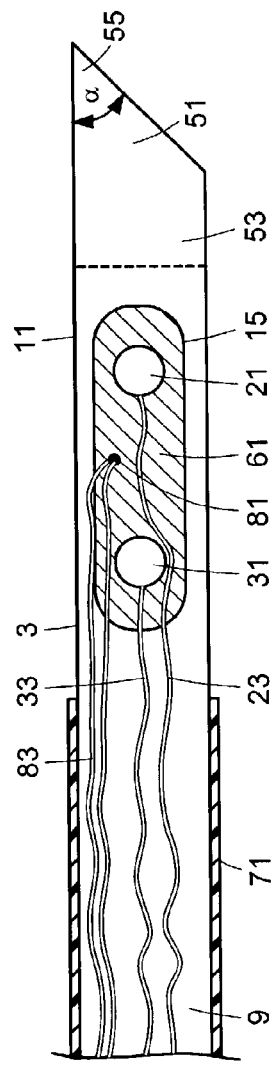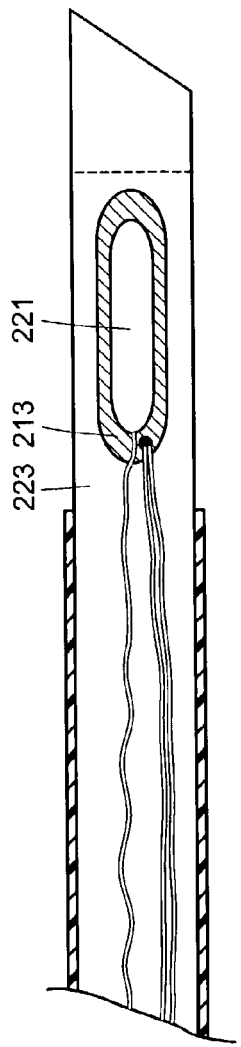

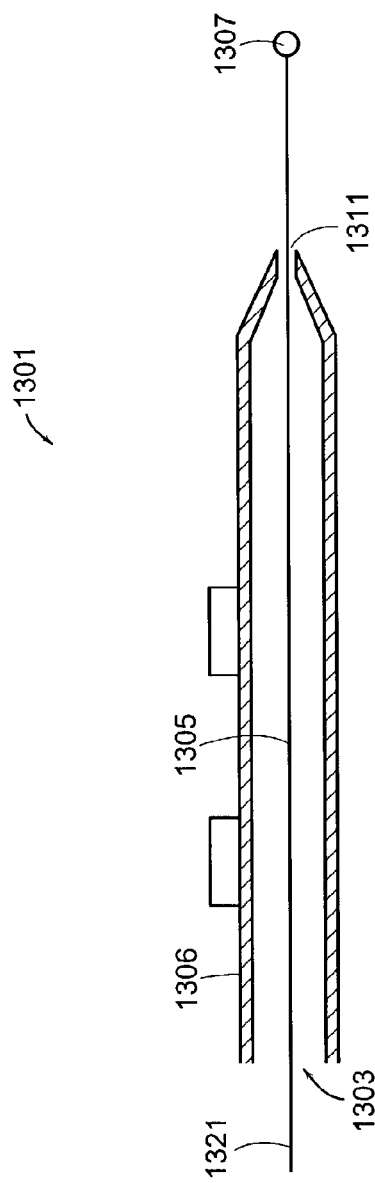

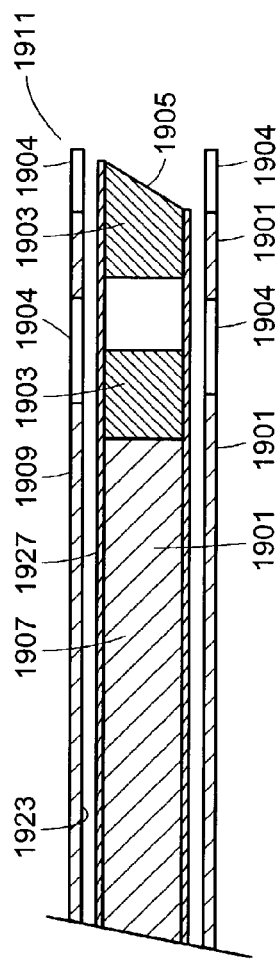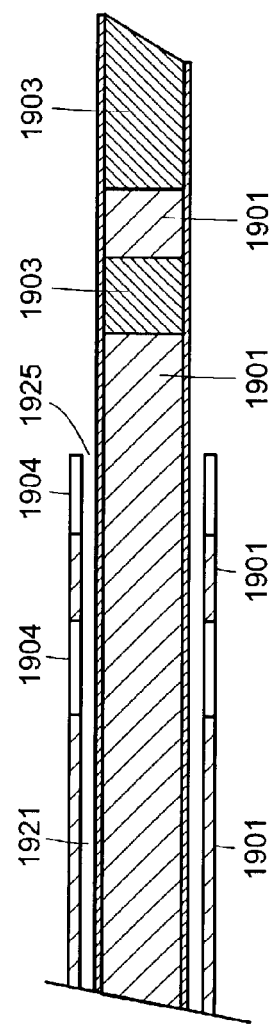

THERMAL DENERVATION DEVICES

CROSS-REFERENCE TO RELATED APPLICATIONS

This application is a continuation of U.S. patent application Ser. No. 12/643,997, now abandoned, filed Dec. 21, 2009, which is a continuation of U.S. patent application Ser. No. 11/745,446, now abandoned, filed on May 7, 2007, which is a continuation of U.S. patent application Ser. No. 10/401,854 filed on Mar. 28, 2003, now U.S. Pat. No. 7,258,690, each of which is incorporated herein by reference in its entirety.

This application is also related to U.S. patent application Ser. No. 10/259,689 filed on Sep. 30, 2002, now U.S. Pat. No. 7,326,203, which is incorporated herein by reference in its entirety.

BACKGROUND OF THE INVENTION

In an effort to reduce back pain through early intervention techniques, some investigators have focused upon nerves contained within the vertebral bodies.

For example, PCT Patent Publication No. WO 01/0157655 ("Heggeness") discloses ablating nerves contained within the vertebral body by first boring into the vertebral body with a nerve ablation device, placing the tip of the device in close proximity to the nerve, and then ablating the nerves with the tip. Heggeness discloses numerous devices, such as electricity transmitting probes, as candidate nerve ablation devices. In describing how to use such a probe, Heggeness discloses "raising the temperature of tip 24 such that the intraosseous nerve is ablated by the heat generated by electrical current passing through tip." See Heggeness at page 8, line 28. The probe disclosed by Heggeness appears to be a solid metal rod functioning as the active electrode of a monopolar RF device.

U.S. Pat. No. 6,478,793 ("Cosman") discloses ablative treatment of metastatic bone tumors, including those within the spine. Pain relief is reportedly achieved by penetrating the bone wall with a suitable probe, and applying heat through the probe to ablate either the bone tumor or the tissue near the bone tumor. Cosman teaches the use of both monopolar and bipolar probes in this application. See Cosman at col. 5, line 44. Cosman also teaches that the treatment may also be used to ablate the nerves and nerve ramifications in and/or around the bone to desensitize them against further tumor encroachment. See Cosman at col. 8, lines 50-65, and col. 9, lines 9-17.

The only probes specifically disclosed by Cosman appear to be monopolar. However, monopolar approaches require the use of a grounding pad beneath the patient and allows energy to flow from the probe and to dissipate in the surrounding tissue. Because the path by which the energy flows from a monopolar probe to its corresponding pad is uncontrolled, the energy may undesirably flow through sensitive tissue, such as the spinal cord. Since this method may cause undesired local muscle or nerve stimulation, it may be difficult or dangerous to operate in sensitive areas of the human body.

Cosman teaches that the electrode may be rigid and robust and capable of piercing bone. Cosman teaches that the electrode may comprise a metal tubular shaft (with appropriate wall thickness to prevent buckling or bending during penetration of hard bone) with a rugged pointed tip. See Cosman at col. 6, lines 34-46. Beyond teaching the use of a generic bipolar probe, Cosman does not disclose any particular bipolar electrode configuration.

U.S. Pat. No. 6,168,593 ("Sharkey") discloses thermal probes in which the electrodes are disposed at an angle to the longitudinal axis of the probe. In one embodiment, an electrode is located in a laterally-disposed window of a tubular, electrically insulating shaft. See FIG. 1A. According to Sharkey, this electrode can ablate tissue at an angle to the principal axis of the probe.

Although the probe disclosed in FIG. 1A of Sharkey appears to be monopolar, Sharkey also teaches that "bipolar delivery can be implemented using the techniques of the current invention by providing at least two distinct elements on the tip, each connected to outgoing and return electrical paths from the RF power supply."

Sharkey does not disclose a return and an active electrode located within the same window. Sharkey does not disclose a window in a conductive shaft. Sharkey does not disclose a probe having a tip adapted to penetrate bone.

U.S. Pat. No. 5,944,715 ("Goble") discloses electrosurgical instruments wherein active electrodes 14 are housed within a window of an insulator. See FIGS. 1 and 4.

Like Sharkey, Goble does not disclose a return and an active electrode located within the same window, nor a window in a conductive shaft, nor a probe having a tip adapted to penetrate bone.

SUMMARY OF THE INVENTION

The present inventors have found that the shaft of a bipolar probe adapted to penetrate bone can be made by simply joining a solid, sharp tip onto a hollow tube. The resulting shaft is of sufficient strength to penetrate the cortical shell of a vertebral body. Furthermore, since the shaft comprises a hollow tube, wires for an electrode can be housed within the tube, thereby allowing a bipolar or sesquipolar configuration. The combination of the ability to penetrate a cortical shell and the ability to provide bipolar or sesquipolar function represents an advance over the conventional technology.

Therefore, in accordance with the present invention, there is provided an electrosurgical device, comprising:
 a) a hollow shaft having an annular wall having a longitudinal bore therein, a proximal portion and a distal portion, and a first window extending transversely through the annular wall, and
 b) a first electrode disposed within the window and being in electrical connection with a power supply, and
 c) a tip having a proximal end portion, a sharp tipped distal end adapted to penetrate cortical bone, the proximal end portion of the tip mechanically connected to the distal portion of the bore of the hollow shaft.

In some embodiments, a space is provided between the tip and tube for ease of manufacturing.

Also in accordance with the present invention, there is provided an electrosurgical device, comprising:
 a) a hollow shaft having an annular wall having a longitudinal bore therein, a proximal portion and a distal portion, and
 b) an electrically insulating spacer having a proximal end and a distal end portion, the proximal end being mechanically connected to the distal portion of the bore of the hollow shaft.

In another aspect of the present invention, the present inventors have found that if the tubular portion of the shaft is made of an electrically conductive material and a window is formed in that tubular portion, then a simple and effective probe can be made by electrically insulating the rim of the window and then placing an electrode within the insulated window. This configuration allows the construction of a bipolar electrode having a simple and low cost design.

Therefore, in accordance with the present invention, there is provided an electrosurgical device, comprising:

a) a hollow shaft having an annular wall having a longitudinal bore therein, a proximal portion and a distal portion, and a first window extending transversely through the annular wall and defining an inside rim, and b) a first electrode disposed within the window and being in electrical connection with a power supply, and c) an electrically insulating material disposed between the inside rim of the first window and the first electrode.

Also in accordance with the present invention, there is provided an electrosurgical device, comprising:

a) a hollow shaft made of an electrically conductive material having an annular wall having a longitudinal bore therein, a proximal portion and a distal portion, and a first window extending transversely through the annular wall, and b) a first electrode disposed within the window and being in electrical connection with a power supply.

In some embodiments, both the return and active electrodes are housed within the same window, thereby further reducing the complexity of the manufacturing process.

Therefore, in accordance with the present invention, there is provided an electrosurgical device, comprising:

a) a hollow shaft having an annular wall having a longitudinal bore therein, a proximal portion and a distal portion, and a first window extending transversely through the annular wall, and b) an active electrode disposed within the window and being in electrical connection with a power supply, and a return electrode disposed within the window and being in electrical connection with the power supply.

DESCRIPTION OF THE FIGURES

FIG. 1 discloses a side view of a device of the present invention having a pair of complementary electrodes housed within a window and electrically isolated from the inside rim of the window by an insulating material.

FIG. 2 discloses a side view of a device of the present invention having a single electrode housed within a window and electrically isolated from the inside rim of the window by an insulating material.

FIG. 5b discloses an exploded view of FIG. 5a.

FIGS. 13a-b are cross-sections of devices of the present invention having slidable temperature probes.

FIGS. 19a and 19b present axial cross-sectional views of a telescoping embodiment of the present invention in which the electrodes are in respective undeployed and deployed configurations.

DETAILED DESCRIPTION OF THE INVENTION

Figure 3:
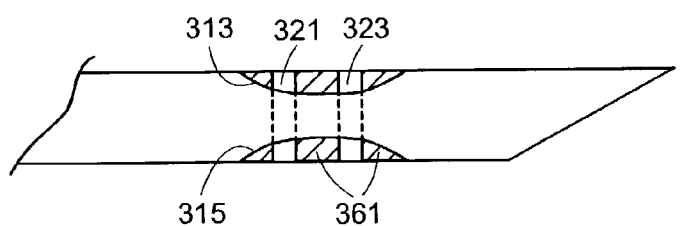
FIG. 3 discloses a side view of a device of the present invention having a pair of electrodes traversing the diameter of the shaft and housed within opposing windows.

For the purposes of the present invention, the "resistive heating zone" is the zone of bone tissue that is resistively heated due to an energy loss incurred by current traveling directly through the bone tissue. Resistive heating, "joule" heating and "near-field" heating may be used interchangeably herein. The "conductive heating zone" is the zone of bone tissue that is heated due to the conduction of heat from an adjacent resistive heating zone. The total heating zone ("THZ") in a bone tissue includes both the resistive heating zone and the conductive heating zone. The border between the conductive and resistive heating zones is defined by the locations where the strength of the electric field is 10% of the maximum strength of the electric field between the electrodes. For the purposes of the present invention, the heating zones encompass the volume of bone tissue heated to at least 42° C. by the present invention. For the purposes of the present invention, the "first and second sides" of a vertebral body are the lateral-lateral sides intersected by the basivertebral nerve ("BVN").

Preferably, the present invention comprises a novel probe adapted for piercing cortical bone and having a novel bipolar electrode configuration. More preferably, the present invention comprises a sharp stainless steel tip of sufficient sharpness to pierce cortical bone that is welded to one end of a hollow stainless steel shaft (or, "hypotube"). More preferably, a slot or window is cut into the distal portion of the shaft, thereby providing a window into which insulated electrodes can be placed. The insulation of the electrodes can be accomplished by providing an insulating material, such as a plastic insert or a potted encapsulant, between the inner rim of the window and the electrode.

This design is advantageous over conventional designs because it provides a relatively inexpensive device that is sufficiently rigid and strong to pierce cortical bone, thereby allowing its use for treating osseous nerves and bone tumors within the bone.

In some embodiments, the outer metal shaft of the inventive probe can be coated with an electrical insulator, such as PTFE to electrically insulate the shaft from the body tissue.

In another embodiment of the present invention, there is provided a radiofrequency (RF) applicator device (or "probe") comprising a hollow rigid tube (such as stainless steel) fitted with a handle at its proximal end and an insulating spacer at its distal end, wherein a portion of the insulating spacer is nested within the distal end of the hollow tube. The proximal end of a distally disposed sharp tip is then nested through the spacer and into the distal end of the hollow tube, thereby imparting electrical isolation and greater strength to the assembled device. Preferably, the hollow tube is adapted to be a first electrode and the tip is adapted to be a second electrode, thereby forming a bipolar heating device adapted for treating hard tissue. Preferably, the device may optionally include channels or ports through which a conductive fluid, such as saline, can be delivered to the heating zone to improve the efficiency of the device.

Now referring to FIG. 1, there is provided an electrosurgical device 1, comprising:
a) a hollow shaft 3 having an annular wall having a longitudinal bore therein, a proximal portion 9 and a distal portion 11, and a first window extending transversely through the annular wall and forming a rim 15, and
b) an active electrode 21 disposed within the window and being in electrical connection with a power supply via first lead 23,
c) a return electrode 31 disposed within the window and being in electrical connection with the power supply via second lead 33,
d) an electrically insulating material 61 disposed between the inside rim of the window and the first electrode,
e) a tip 51 having a solid proximal end 53 and a sharp tipped distal end 55 adapted to penetrate cortical bone, the proximal end of the tip being mechanically connected to the distal portion of the bore of the hollow shaft,
f) an outer insulating shell 71 surrounding the proximal portion of the hollow shaft,
g) a thermocouple 81 disposed within the electrically insulating material and being in electrical connection with a digital thermometer via third pair of leads 83.

The shaft of the present invention preferably comprises a hollow tube that allows at least one lead wire to be run therethrough. The material selection and dimensions of the shaft should be selected so as to allow the shaft to support the penetration of the cortical bone by the tip without yielding. Typically, the shaft is made of a metallic or ceramic material. Preferably, the shaft is made of a conductive material, such as a metal. Preferably, the metallic shaft material is selected from the group consisting of stainless steel, titanium, titanium-containing alloys, such as nitinol, copper, and copper plated with gold or platinum. More preferably, the metallic shaft material is stainless steel. In some embodiments, the shaft has a length of between 3 and 20 cm (preferably between 5 cm and 12 cm, an inner diameter of between 0.5 and 5 mm (preferably between 5 and 3 mm), and an outer diameter of between 1 and 6 mm (preferably between 2.0 and 4 mm). When the dimensions of the shaft are within these ranges, conventional biomaterials such as stainless steel can be suitably used.

In some embodiments, the proximal end of the spacer is received over the distal end of the shaft.

The function of the electrodes of the present invention is to be in direct contact with tissue and provide a pathway for RF current through a portion of the tissue surrounding the probe, thereby therapeutically heating the tissue. The electrodes are typically made of metals, such as stainless steel, platinum, gold, copper (nickel-plated or gold-plated), platinum, or a conductive polymer (such as a carbon- or silver-filled epoxy). Preferably, the electrode material of construction is such that its coefficient of thermal expansion is within 50% of the coefficient of thermal expansion of the material selected as the insulator 61.

The function of the insulating annulus of the present invention is to electrically insulate the electrodes located within the window from the electrically conductive shaft. The insulating annulus is typically made of PTFE, nylon, an epoxy, a polyurethane, a polyimide, or other suitable polymer, or a ceramic material.

Preferably, tip 51 provides two functions. First, its sharp tipped distal end 55 should be sufficiently pointed to penetrate cortical bone. Accordingly, although angle α may be any angle between about 0 degrees and about 90 degrees, angle α is preferably between 20 and 70 degrees. When the tip angle is below this range, the tip may be fragile and may be susceptible to breaking during cortical rim penetration. When the angle is above this range, the tip is too blunt and may require excessive force to achieve cortical rim penetration. In some embodiments, the proximal portion of the tip is solid, thereby providing additional strength to the tip. In some embodiments, the proximal portion of the tip has a diameter that substantially the same as the outer diameter of the shaft. In this condition, the proximal portion of the tip may be mechanically joined to the distal end of the shaft (for example, by welding) to produce a strong, streamlined probe.

In other embodiments, the sharp tipped distal end is formed near the axial center of the tip to produce a conical shape.

In some embodiments, the device further comprises an outer insulating sleeve (such as sleeve 71) surrounding at least the proximal portion of the hollow shaft. The function of the sleeve is to electrically isolate the device from the tissue that is adjacent the target tissue, thereby increasing the safety and effectiveness of the device. In some embodiments, the material of construction for the sleeve is selected from the group consisting of polymeric materials such as PTFE and ceramic materials such as alumina. In some embodiments, the sleeve is provided in the form of a coating upon the shaft. In other embodiments, the sleeve is manufactured separately and slid over the shaft. Typically, the sleeve has a length that is between 50% and 95% of the length of the shaft length. In some embodiments, the sleeve extends distally towards the window and terminates within one length of the window.

In some embodiments, the thermocouple is coupled to the power supply in a feedback loop to modulate the power output and thereby control the temperature at the tip.

Now referring to FIG. 2, in other embodiments, the device of FIG. 1 could be modified so that shaft window 213 houses only a single electrode 221. In this instance, the conductive shaft could be electrically connected to the power supply via a handle (not shown) to become the second electrode 223 of a bipolar design. The advantage of having only a single electrode within the window is that the area of the window can be decreased, thereby enhancing the strength of the shaft. When only a single electrode is located within the window, the surface area of that electrode is generally between 0.5 and 20 mm$^2$. This is advantageous in applications requiring relatively larger surface area electrodes. In such embodiments, this embodiment can capably accommodate the larger surface area electrode without increasing window area. In some embodiments, the single windowed electrode could be the active electrode, while in others it could be the return electrode. In some embodiments, the single windowed electrode is the active and has a surface area of between 0.5 and 20 mm$^2$.

In this configuration, the placement of an insulating sleeve preferably provides a distal uninsulated portion of the shaft having a length of between 3 mm and 20 mm, and is more preferably about 5 mm. In preferred embodiments thereof, the insulation is selected from the group consisting of polyimide tape, PTFE tape, and heat shrink tubing. One preferred thickness of the insulation ranges from about 0.006 mm to about 0.012 mm) (i.e., about 0.00025 to 0.0005 inches), and is provided by a dielectric coating, such as a polyimide coating.

Now referring to FIG. 3, in other embodiments, the device of FIG. 1 could be modified to include a pair of windows 313,315 located on opposite sides of the shaft. In such an embodiment, the electrodes 321,323 and insulator 361 could be modified to essentially traverse the bore and connect the windows. This embodiment advantageously allows the clinician to treat target zones on either side of the device, and so is advantageous in instances in which the device is placed within a target tissue such as a tumor.

Alternatively, in some embodiments, neither electrode completely traverses the transverse width of the tube. In some embodiments thereof, each electrode opens through a window on the same side of the tube. In other embodiments thereof, a first electrode opens through a first window on a first side of the tube, and a second electrode opens through a second window on a second side of the tube, preferably on a diametrically opposed side of the tube.

Figure 4:
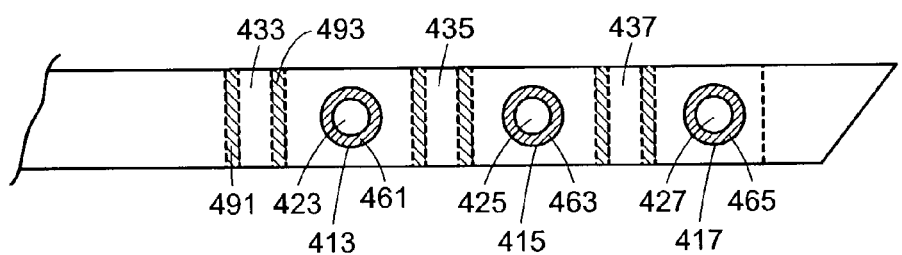
FIG. 4 discloses a side view of the present invention having a plurality of electrodes housed within a plurality of windows.

Now referring to FIG. 4, in other embodiments, the device of FIG. 1 could be modified to include a plurality of windows 413, 415, 417 spaced along the length of the shaft, wherein each window has at least one electrode 423, 425, 427 located therein. Each of these windows is electrically isolated from the conductive shaft by an insulating annulus 461, 463, 465. The provision of multiple windowed electrodes allows the surgeon the ability to either treat different zones at different times without needing to move the device, or to treat a larger area. In some embodiments having a series of windows (not shown), both the return and active electrodes can be located within the same window. In other embodiments, each window houses a single (preferably, active) electrode, and the second (preferably, return) electrode 433,435,437 is provided on the surface of the electrically conductive shaft between bands of insulating material. In other embodiments, the second return electrode is provided by another windowed electrode. Thus, the surgeon can select any pair of electrode to define the treatment area. In this particular embodiment, return electrode 433 is electrically connected to the power supply via an internal lead (not shown) and is electrically isolated from the remainder of the shaft by insulating windows comprising left side portion 491 and right side portion 493.

Figure 5A:
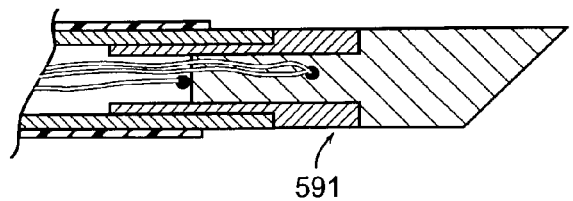
FIG. 5a discloses a side view of a device of the present invention in which the device has been longitudinally cross-sectioned to reveal nesting features.
Figure 5B:
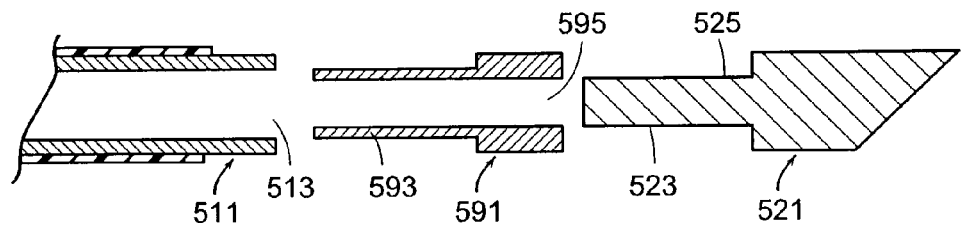

In some embodiments, and now referring to FIGS. 5a and 5b, an intermediate spacer 591 is provided between the shaft 511 and the sharp tip 521. When this spacer is made of an electrically insulating material, the sharp tip 521 could be adapted to function as the first electrode. In some embodiments thereof, the shaft 511 could be adapted to function as the second electrode. The use of the tip and shaft as paired electrodes is advantageous because of its simplicity of design and assembly, and its larger active surface area.

In some embodiments, as in FIGS. 5a and 5b, the insulating spacer is hollow. The hollow nature of the spacer allows a lead wire to run therethrough and electrically connect the sharp tip to the power supply, and also allows the proximal end 523 of the tip to be nested in the hollow distal portion 595 of the spacer. In these FIGS. 5a and 5b, the proximal end portion 593 of the hollow spacer is nested within the distal end portion 513 of the conductive shaft.

The robust nature of the embodiment shown in FIG. 5a could be further enhanced by proximally extending the nested portion of the hollow spacer sufficiently deep into the distal portion of the shaft, thereby providing increased surface area for bonding.

Similarly, the proximal end portion 523 of the sharp tip (the distal half 525 of which is preferably solid) can be made to extend so far proximally as to nest in the conductive shaft. Because the intervening spacer is made of an electrically insulating material, the conductive tip is electrically isolated from the conductive shaft. The proximal extension of the tip into the shaft likewise increases the robust nature of the probe.

Figure 6:
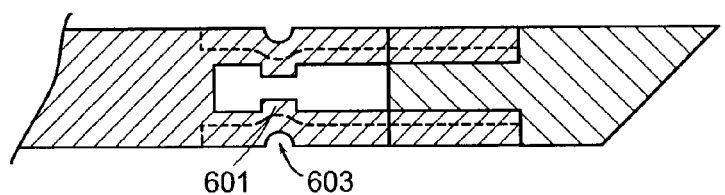
FIG. 6 discloses a cross-sectional view of a device of the present invention having a grooved distal tip and a crimped shaft.

Now referring to FIG. 6, the robust nature of the probe could be further fortified to prevent tip pull-out by providing a circumferential groove 601 in the nested portion of the solid tip and providing a swage or crimp 603 in the portion of the outer shaft overlying the groove. In such embodiments, the intervening insulating spacer should be made of a material sufficiently malleable to accept crimping or swaging.

Figure 7:
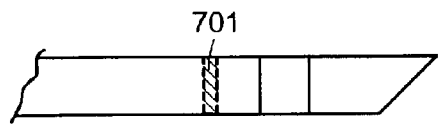
FIG. 7 discloses a cross-sectional view of a device of the present invention having a throughhole traversing the distal tip and shaft and filled with a bonding material.

Now referring to FIG. 7, the robust nature of the probe could be further fortified to prevent tip pull-out by providing a transverse through-hole 701 through the probe in the area of the nested portion of the solid tip and then filling the through-hole with a bonding material such as an adhesive such as epoxy, or with an electrically non-conductive locking pin or screw.

Figure 8A:
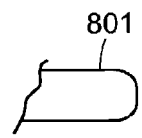
FIGS. 8a and 8b disclose distal tips of the present invention having chamfered features.
Figure 8B:
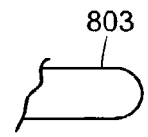
Figure 9A:
FIGS. 9a-f disclose a circular transverse cross-sections of the sharp tip.
Figure 9B:
Figure 9C:
Figure 9D:
Figure 9E:
Figure 9F:

Now referring to FIG. 8a, in some embodiments, it may be desirable to provide a tapered feature 801 upon the distal end of the sharp tip. Providing such a tapered feature is advantageous because a) it will prevent the device from penetrating through the anterior cortical wall of the vertebral body, and b) it will reduce current density at the electrode tip and minimize regions of excessive current density, thereby providing an even heating zone. In some embodiments, as in FIG. 8a, the tapered feature comprises a chamfer. In others, as in FIG. 8b, the tapered feature is more substantial and preferably comprises an essentially 180 degree rounded curve, such as a semicircle or a bullet nose 803.

Now referring to FIGS. 9a-9f, in some embodiments, the transverse cross section of the sharp tip is acircular. The acircular cross-section may allow the clinician to generate differently shaped heating profiles, or to access different anatomies (such as between tissue planes, or to follow specific tissue contours (i.e., between the intervertebral disc and spinal cord). In some preferred embodiments, the acircular cross section is selected from the group consisting of rounded (as in FIG. 9a), oval (as in FIG. 9b), elliptical (as in FIG. 9c), bilobular (as in FIG. 9d), arc-like (as in FIG. 9e) and s-shaped (as in FIG. 9f).

If the active electrode has no active cooling means, it may become be subject to conductive heating induced by the heated tissue, and the resultant increased temperature at the electrode-tissue interface in the electrode may adversely affect performance by charring the adjacent bone tissue. Accordingly, in some embodiments, a cool tip active electrode may be employed. The cooled electrode helps maintain the temperature of the electrode at a desired temperature. Cooled tip active electrodes are known in the art. Alternatively, the power supply may be designed to provided a pulsed energy input. It has been found that pulsing the current favorably allows heat to dissipate from the electrode tip, and so the active electrode stays relatively cooler.

Figure 10:
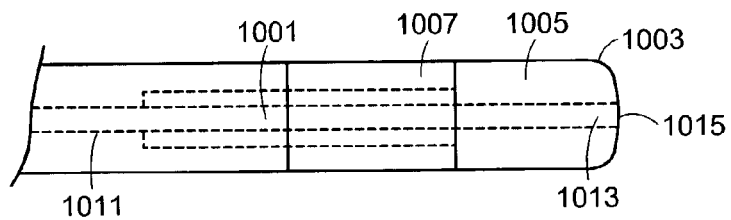
FIG. 10 discloses a device of the present invention having a means for delivering fluid that delivers fluid through an opening on the surface of the distal tip.

In some embodiments, and now referring to FIG. 10, it may also be desirable to provide a means for delivering a fluid to the distal end of the device. The fluid may be a cooling fluid that will help control the heating activity, or it may be a carrier for therapeutic agents such as drugs, or provide an electrolyte solution (such as isotonic or hypertonic saline) for efficient current flow. In some embodiments, providing the means for delivering a fluid could be accomplished by providing a longitudinal fluid delivery tube 1001 extending from the tubular portion of the shaft to the outer surface 1003 of either the sharp tip 1005 or insulating spacer 1007. Preferably, the fluid delivery tube has a proximal portion 1011 extending into the tubular portion of the shaft and a distal portion 1013 opening onto the outer surface 1015 of the sharp distal tip.

In some embodiments, as in FIG. 10, the fluid delivery tube is provided as a separate physical entity. In other embodiments, the fluid delivery tube is made by simply providing longitudinal, fluidly connected holes in the other components.

Figure 11:
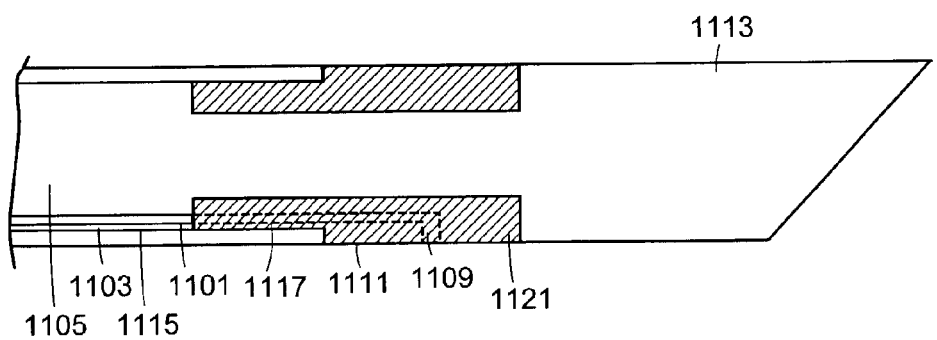
FIG. 11 discloses a device of the present invention having a means for delivering fluid that delivers fluid through an opening on the surface of the insulating spacer.

Now referring to FIG. 11, in some embodiments in which the sharp tip 1113 also acts as an electrode, the fluid delivery tube 1101 has a proximal portion 1103 extending into the tubular portion 1105 of the shaft and a distal opening portion 1109 opening onto the outer surface 1111 of the insulating spacer. In these embodiments, the spacer acts not only as a conduit for fluid delivery, it still provides electrical insulation between the sharp tip electrode and the shaft-based electrode. In some embodiments, as in FIG. 11, the fluid delivery tube can comprise a separate physical entity portion 1115 and a portion 1117 produced by making a hole in an already existing component (such as spacer 1121).

Figure 12A:
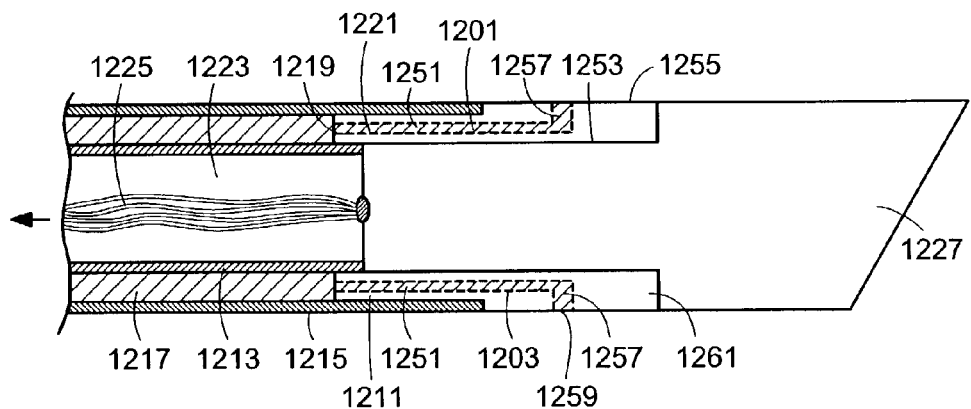
FIG. 12a discloses a device of the present invention having a means for delivering fluid that delivers fluid through a plurality of openings on the surface of the insulating spacer.
Figure 12B:
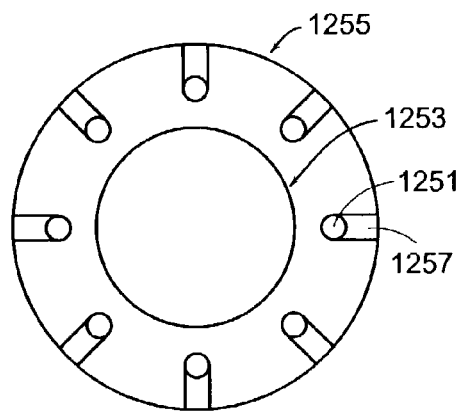
FIG. 12b discloses a transverse cross section of FIG. 12a, taken through the spacer.

Now referring to FIG. 12*a*, in some embodiments, multiple fluid delivery tubes 1201, 1203 are used. In these embodiments, conductive efficiency is enhanced because the multiple fluid delivery tubes may now deliver fluid all about the radius of the device, as shown in cross-sectional FIG. 12*b*. FIG. 12*b* is a cross-section of FIG. 12 a taken transversely through the spacer. In FIG. 12*b*, longitudinal hole portions 1251 are provided between the inner 1253 and outer 1255 diameters of the spacer to deliver fluid from within the shaft, while radially extending hole portions 1257 extend radially from the longitudinal hole portions and deliver fluid to the outer surface 1259 of the spacer 1261.

In some embodiments, thermocouples are placed in radially extending hole portions of the fluid delivery tubes in order to monitor the surface temperature of the device at various radial locations. In these embodiments, the fluid delivery tube having a thermocouple therein is effectively blocked so that each tube has either a thermocouple or fluid delivery function, but not both.

Also as shown in this embodiment, the proximal portion 1211 of each fluid delivery tube can comprise a single inner wall 1213 and a single outer wall 1215 defining a single large diameter annulus 1217 therebetween. Fluid is delivered through this annulus to the proximal portion 1219 of the plurality of holes 1221 provided in the insulating spacer.

The annular nature of the proximal portion of the fluid delivery tube is also advantageous because it also provides a convenient inner tube 1223 through which a lead 1225 can be run to electrically connect the sharp tip 1227 to the power supply.

In general, it is desirable to operate the present invention in a manner that produces a peak temperature in the target tissue of between about 80° C. and 100° C. When the peak temperature is below 80° C., the off-peak temperatures may quickly fall below about 45° C. When the peak temperature is above about 100° C., the bone tissue exposed to that peak temperature may experience necrosis and charring. This charring reduces the electrical conductivity of the charred tissue, thereby making it more difficult to pass RF current through the target tissue beyond the char and to resistively heat the target tissue beyond the char. In some embodiments, the peak temperature is preferably between 90° C. and 98° C.

It is desirable to heat the volume of target tissue to a minimum temperature of at least 42° C. When the tissue experiences a temperature above 42° C., nerves within the target tissue may be desirably, damaged. However, it is believed that denervation is a function of the total quantum of energy delivered to the target tissue, i.e., both exposure temperature and exposure time determine the total dose of energy delivered. Accordingly, if the temperature of the target tissue reaches only about 42° C., then it is believed that the exposure time of the volume of target tissue to that temperature should be at least about 30 minutes and preferably at least 60 minutes in order to deliver the dose of energy believed necessary to denervate the nerves within the target tissue.

Preferably, it is desirable to heat the volume of target tissue to a minimum temperature of at least 50° C. If the temperature of the target tissue reaches about 50° C., then it is believed that the exposure time of the volume of target tissue to that temperature need only be in the range of about 2 minutes to 10 minutes to achieve denervation.

More preferably, it is desirable to heat the volume of target tissue to a minimum temperature of at least 60° C. If the temperature of the target tissue reaches about 60° C., then it is believed that the exposure time of the volume of target tissue to that temperature need only be in the range of about 0.5 minutes to 3 minutes to achieve denervation, preferably 1 minute to 2 minutes.

Typically, the period of time that an intraosseous nerve ("ION") is exposed to therapeutic temperatures is in general related to the length of time in which the electrodes are at the target temperature following heat up. However, since it has been observed that the total heating zone remains relatively hot even after power has been turned off (and the electric field eliminated), the exposure time can include a period of time in which current is not running through the electrodes.

In some embodiments, it is desirable to heat the target tissue so that at least about 1 $cm^3$ of bone tissue experiences the minimum temperature. This volume corresponds to a sphere having a radius of about 0.6 cm. Alternatively stated, it is desirable to heat the target tissue so the minimum temperature is achieved by every portion of the bone within 0.6 cm of the point experiencing the peak temperature.

More preferably, it is desirable to heat the target tissue so that at least about 3 $cm^3$ of bone experiences the minimum temperature. This volume corresponds to a sphere having a radius of about 1 cm.

In one preferred embodiment, the present invention provides a steady-state heated zone having a peak temperature of between 80° C. and 100° C. (and preferably between 90° C. and 98° C.), and heats at least 1 $cm^3$ of bone (and preferably at least 3 $cm^3$ of bone) to a temperature of at least 50° C. (and preferably at least 60° C.).

As noted above, a peak temperature below about 100° C. is desirable in order to prevent charring of the adjacent tissue, steam formation and tissue popping. In some embodiments, this is accomplished by providing the power supply with a feedback means that allows the peak temperature within the heating zone to be maintained at a desired target temperature, such as 90-98° C. In some embodiments, between about 10 watts and 30 watts of power is first supplied to the device in order to rapidly heat the relatively cool bone, with maximum amperage being obtained within about 10 15 seconds. As the bone is further heated to the target temperature, the feedback means gradually reduces the power input to the device to between about 6 10 watts.

Although preferred embodiments of the present invention typically comprises bipolar electrodes, the probes of the present invention can be easily adapted to provide monopolar use. For example, the device of FIG. 2 could be modified so that the shaft is electrically isolated at the handle, and a ground electrode is provided to extend from the power supply to the patient.

The following section relates to the general structure of preferred energy devices in accordance with the present invention:

The apparatus according to the present invention comprises an electrosurgical probe having a shaft with a proximal end, a distal end, and at least one active electrode at or near the distal end. A connector is provided at or near the proximal end of the shaft for electrically coupling the active electrode to a high frequency voltage source. In some embodiments, a return electrode coupled to the voltage source is spaced a sufficient distance from the active electrode to substantially avoid or minimize current shorting therebetween. The return electrode may be provided integral with the shaft of the probe or it may be separate from the shaft.

In preferred embodiments, the electrosurgical device will comprise a shaft or a handpiece having a proximal end and a distal end which supports one or more electrodes. The shaft may assume a wide variety of configurations, with the primary purpose being to mechanically support the active electrode and permit the treating physician to manipulate the electrode from a proximal end of the shaft. The shaft may be rigid or flexible, with flexible shafts optionally being combined with a generally rigid external tube for mechanical support. Flexible shafts may be combined with pull wires, shape memory actuators, and other known mechanisms for effecting selective deflection of the distal end of the shaft to facilitate positioning of the electrode array. The shaft may include a plurality of wires or other conductive elements running axially therethrough to permit connection of the electrode array to a connector at the proximal end of the shaft.

In some embodiments, the shaft comprises a hollow annulus adapted to be introduced through a posterior percutaneous penetration in the patient. Thus, the shaft adapted for posterior percutaneous use may have a length in the range of about 3 to 25 cm (preferably, 12-15 cm), and a diameter in the range of about 1 mm to about 6 mm (preferably, 2-5 mm). However, for endoscopic procedures within the spine, the shaft will have a suitable diameter and length to allow the surgeon to reach the target site (e.g., a disc) by delivering the shaft through the thoracic cavity, the abdomen or the like. Thus, the shaft may have a length in the range of about 5.0 to 30.0 cm, and a diameter in the range of about 1 mm to about 6 mm (preferably, about 2 mm to about 4 mm). In any of these embodiments, the shaft may also be introduced through rigid or flexible endoscopes.

The probe further comprises one or more active electrode(s) for applying electrical energy to the cancellous region of the vertebral body. The probe may be bipolar and include one or more return electrode(s). In some embodiments thereof, the bipolar probe has an active electrode array disposed at its distal end. In other embodiments, the probe may be monopolar, whereby the return electrode may be positioned on the patient's back, as a dispersive pad. In either embodiment, sufficient electrical energy is applied through the probe to the active electrode(s) to heat the tissue in the target area and thereby denervate at least a portion of the basivertebral nerve within the vertebral body.

In some embodiments, the probe that is delivered percutaneously and/or endoluminally into the patient by insertion through a conventional or specialized guide catheter. The catheter shaft may include a guide wire for guiding the catheter to the target site, or the catheter may comprise a steerable guide catheter. The catheter may also include a substantially rigid distal end portion to increase the torque control of the distal end portion as the catheter is advanced further into the patient's body.

In some embodiments, the electrically conductive wires may run freely inside the catheter bore in an unconstrained made, or within multiple lumens within the catheter bore.

In some embodiments, the tip region of the device may comprise many independent electrode terminals designed to deliver electrical energy in the vicinity of the tip. The selective application of electrical energy is achieved by connecting each individual electrode terminal and the return electrode to a power source having independently controlled or current limited channels. The return electrode(s) may comprise a single tubular member of conductive material proximal to the electrode array. Alternatively, the instrument may comprise an array of return electrodes at the distal tip of the instrument (together with the active electrodes) to maintain the electric current at the tip. The application of high frequency voltage between the return electrode(s) and the electrode array results in the generation of high electric field intensities at the distal tips of the electrode terminals with conduction of high frequency current from each individual electrode terminal to the return electrode. The current flow from each individual electrode terminal to the return electrode(s) is controlled by either active or passive means, or a combination thereof, to deliver electrical energy to the surrounding conductive fluid while minimizing energy delivery to surrounding (non-target) tissue.

In some embodiments, the device further comprises at least one temperature probe. The temperature is preferably selected from the group consisting of a thermocouple, a thermistor, and a fiber-optic probe (and is preferably a thermocouple). Thermocouples associated with the device may preferably be disposed on or within the electrode carrier; between the electrodes (preferred in bipolar embodiments); or within the electrodes (preferred for monopolar embodiments). In some embodiments wherein the electrodes are placed on either side of the basivertebral nerve, a thermocouple is disposed between the electrodes or in the electrodes. In alternate embodiments, the deployable portion of the thermocouple comprises a memory metal.

One common characteristic of conventional thermal therapy devices is the dimensionally fixed nature of the temperature probe. Because of this fixed nature, the temperature probe can not be moved relative to the shaft, and so can not provide spatially-changing analysis unless the shaft is moved as well. Because it is often problematic to move the shaft, the fixed nature of the probe limits the extent of temperature analysis.

Now referring to FIG. 13a, in one aspect of the present invention, there is provided a thermal therapy device 1301 having a sliding temperature probe. An axial bore 1303 is provided in the shaft 1306 of the present invention, and an elongate carrier 1305 having a probe 1307 disposed thereon is placed within the bore for slidable movement within the bore. Because the carrier is slidable, the temperature probe may be moved to different axial locations along the axis of the shaft by simply pushing or pulling the proximal end portion 1321 of the carrier, thereby providing the clinician with the ability to easily measure temperature at any selected axial location.

In this particular instance, the distal end of the shaft has an opening 1311, thereby allowing the probe to record temperatures outside of the shaft.

Therefore, in accordance with the present invention, there is provided a thermal therapy device comprising:
  a) a hollow shaft having an annular wall having an outer surface and a longitudinal bore therein, the longitudinal bore being in communication with an opening upon the outer surface,
  b) a first electrode disposed on or within the shaft and being in electrical connection with a power supply, and
  c) a thermal probe having a elongate carrier and a thermal sensor disposed on the carrier, wherein the carrier is slidably disposed within the longitudinal bore.

Figure 13B:
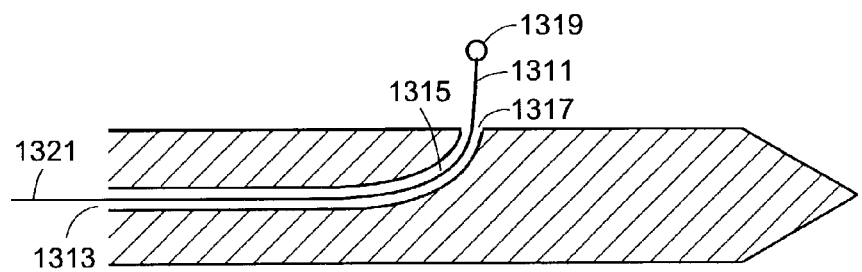

Although the device of FIG. 13*a* is useful in providing temperature information along the shaft axis, it can not provide off-axis information. Accordingly, in one preferred embodiment of the slidable probe, and now referring to FIG. 13*b*, the carrier 1311 is made of a memory metal material. As before, an axial bore is provided in the proximal portion of the shaft. However, in this embodiment, while the proximal portion 1313 of the bore is linear, the distal portion 1315 of the bore curves to open onto the surface of the shaft through opening 1317, thereby providing a curved bore. An elongate carrier 1311 made of a memory metal having a probe 1319 disposed thereon is placed within the bore for slidable movement within the bore. Because the carrier is made of a memory metal, the temperature probe may be moved to different off-axis locations by simply pushing or pulling the proximal end portion 1321 of the carrier, thereby providing the clinician with an even greater ability measure temperature radially around the device. In some embodiments, the temperature probe 1319 of FIG. 13*b* is located at the edge of the target zone to insure that the targeted zone is sufficiently dosed.

The temperature probe shown in FIG. 13*a* is located along the central axis of the shaft of the device. Although this central axial location provides ease of manufacture, the ability of the probe to record the actual tissue temperature may be diminished due to the fact that the probe is not actually in the tissue, but rather in he center of the therapeutic device.

Figure 13C:
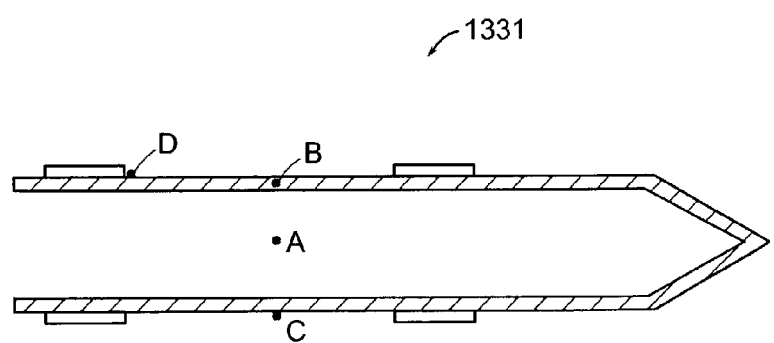
FIG. 13c is a cross-section depicting various preferred locations for a temperature probe of a device of the present invention.

Therefore, is some embodiments of the present invention, there is provided a thermal therapy device 1331 having an axially-offset temperature probe. Now referring to FIG. 13*c*, there are provided i) a first temperature probe A located within the central axis of the shaft; ii) a second temperature probe B located within the outer wall of the shaft; iii) a third temperature probe C located on the outer surface of the wall of the shaft (i.e., at the wall/tissue interface); and iv) a fourth temperature probe D located on the outer surface of the wall and at the electrode/insulator interface.

Locating the probe a position A allows the device to be easily manufactured. Locating temperature probe B located within the outer wall of the shaft allows the device to be easily manufactured and durable, and avoids biocompatibility issues. Locating third temperature probe C at the wall/tissue interface provides the most realistic estimate of the tissue temperature. Locating fourth temperature probe D at the electrode/insulator interface allows the device to be easily manufactured a provides measurement of a relatively hot region.

In general, bipolar and monopolar electrodes are used to apply a thermal therapy to tissue for a therapeutic effect. Many probes are actively temperature controlled to monitor and apply a certain thermal dose. Also, electrodes are often cooled (internally) to prevent charring near or on the probe tip and thus allow more power to hear tissue further away from the tip and to create a larger treatment zone. One major drawback to this type of device is that the system is not able monitor the temperature of the lesion. It only monitors the tip temperature, which is being cooled to 0° C., to allow more power to be put into the tissue and create a larger lesion.

Figure 14A:
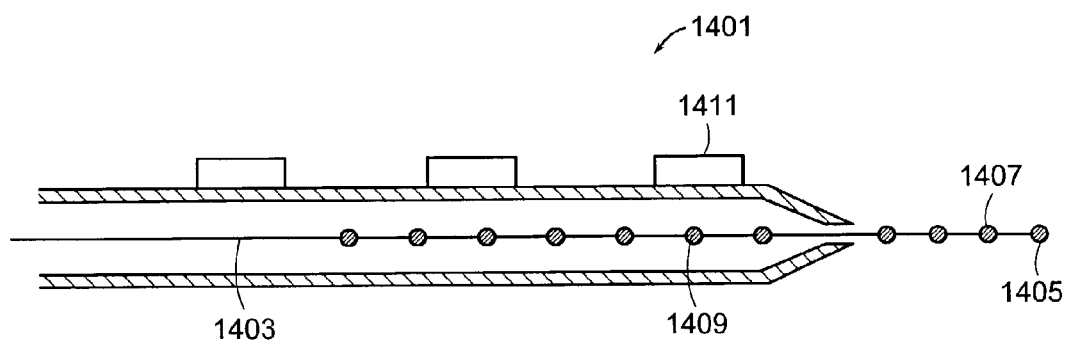
FIGS. 14a-b are cross-sections of devices of the present invention having multi-sensor temperature probes.

In one embodiment of the present invention, and now referring to FIG. 14*a*, there is provided a thermal therapy device 1401 having a multi-sensor temperature probe comprising a carrier 1403 and a plurality of temperature sensors 1405, 1407 that deploys into the tissue to monitor heating and thermal dose directly distal of the tip. In some embodiments, a sensor 1409 is also provided on the carrier to monitor temperatures in the vicinity of the electrodes 1411. In use, once the device is placed in the tissue, the linear multisensor temperature probe is deployed away from the surface of the probe. Preferably, adjacent multisensors such as 1405 and 1407 are placed about 5 mm apart from each other to give adequate data for temperature distribution within the tissue.

Figure 14B:
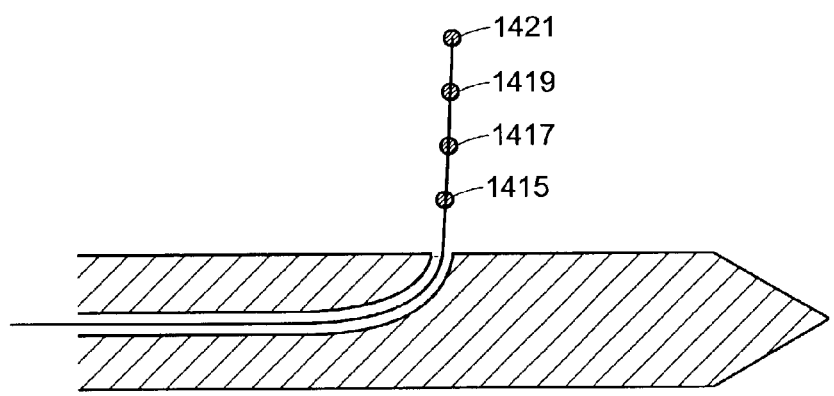

Now referring to FIG. 14*b*, there is provided a multisensor temperature probe as in FIG. 14*a*, but the carrier is made of a memory metal, thereby allowing the carrier to deploy from a side wall of the shaft and allowing the clinician to record off-axis temperature data simultaneously from sensors 1415, 1417, 1419 and 1421 at a plurality of different locations.

The electrode terminal(s) are preferably supported within or by an insulating support positioned near the distal end of the device. The return electrode(s) may be located on the instrument shaft, on another instrument, or on the external surface of the patient (i.e., a dispersive pad). The return electrode is preferably integrated with the shaft. The proximal end of the shaft preferably includes the appropriate electrical connections for coupling the return electrode(s) and the electrode terminal(s) to a high frequency power supply, such as an electrosurgical generator.

In some embodiments, the distal end of the device has surface geometries shaped to promote the electric field intensity and associated current density along the leading edges of the electrodes. Suitable surface geometries may be obtained by creating electrode shapes that include preferential sharp edges, indented grooves, or by creating asperities or other surface roughness on the active surface(s) of the electrodes. Surface shapes according to the present invention can include the use of formed wire (e.g., by drawing round wire through a shaping die) to form electrodes with a variety of cross-sectional shapes, such as square, rectangular, L or V shaped, or the like. Edges may also be created by removing a portion of the elongate metal shaft to reshape the cross-section. For example, material can be ground along the length of a round or hollow shaft electrode to form D or C shaped electrodes, respectively, with edges facing in the cutting direction. Alternatively, material can be removed at closely spaced intervals along the shaft length to form transverse grooves, slots, threads or the like along the electrodes. In other embodiments, the shaft can be sectored so that a given circumference comprises an electrode region and an inactive region. In some embodiments, the inactive region is masked.

The return electrode is preferably spaced proximally from the active electrode(s) a suitable distance. In most of the embodiments described herein, the distal edge of the exposed surface of the return electrode is spaced about 2 to 25 mm from the proximal edge of the exposed surface of the active electrode(s). This distance may vary with different voltage ranges, the electrode geometry and depend on the proximity of tissue structures to active and return electrodes. The return electrode will typically have an exposed length in the range of about 1 to 20 mm. Preferably, the ratio of the exposed length of the return electrode to the active length of the active electrode is at least 2:1.

The present invention may use a single active electrode terminal or an array of electrode terminals spaced around the distal surface of the shaft. In the latter embodiment, the electrode array usually includes a plurality of independently current-limited and/or power-controlled electrode terminals to apply electrical energy selectively to the target tissue while limiting the unwanted application of electrical energy to the surrounding tissue and environment resulting from power dissipation into surrounding electrically conductive fluids, such as blood, normal saline, and the like. The electrode terminals may be independently current-limited by isolating the terminals from each other and connecting each terminal to a separate power source that is isolated from the other electrode terminals. Alternatively, the electrode terminals may be connected to each other at either the proximal or distal ends of the shaft to form a single wire that couples to a power source. Alternatively, different electrode terminals can be selected to be active, thereby modifying the path of current and subsequent lesion size and location.

In some embodiments, the plurality of active electrodes are radially staggered about the cross-section of the shaft. In some embodiments, the radially staggered electrodes are individually controllable.

Figure 15A:
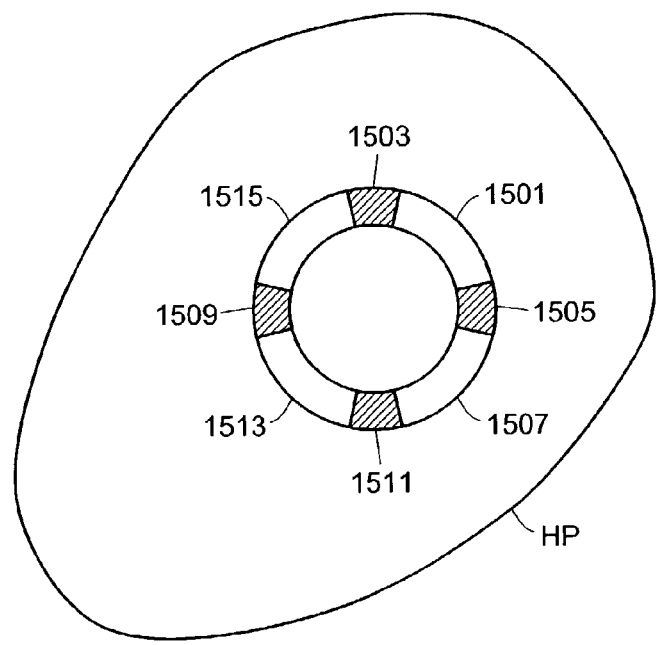
FIG. 15a is a cross-section of a device of the present invention having radially segmented electrodes.

Now referring to FIG. 15a, there is provided a transverse cross-sectional view of a device of the present invention having a preferred active electrode configuration. This configuration alternates the active electrodes 1501, 1507, 1513, 1515 between insulating elements 1505, 1511, 1509, 1503. The electrodes could be connected such that 1513 was active and the grouping of 1515, 1507 and 1501 was connected to the return of the RF source. This would influence the heating pattern as shown in FIG. 15a. Other modes of operation would be to connect 1513 to active and 1501 to return, or 1513 and 1501 to active and 1507 and 1515 to ground. Any of several connections will allow for slight changes in the heating pattern HP. In addition, the active electrodes could be multiplexed in time such that 1513 and 1501 would be connected to active and return, respectively for 1 to 10 seconds and then 1515 and 1507 would be connected to active and return for 1 to 10 seconds. In this way, the heating pattern can be manipulated to provide longer heating times for selected combinations, thereby increasing the temperature of the targeted tissue. The electrodes could also be made operational in a monopolar fashion, such that an electrode (i.e., 1515 or 1501) would be active for a period of time and then another electrode would be switched on. Another embodiment would be to connect any combination of one, two, three or four electrodes to active and the return would be remote on the patient. Any of these combinations could also be multiplexed in time or have greater or lesser voltages to create more or less heating, respectively.

Figure 15B:
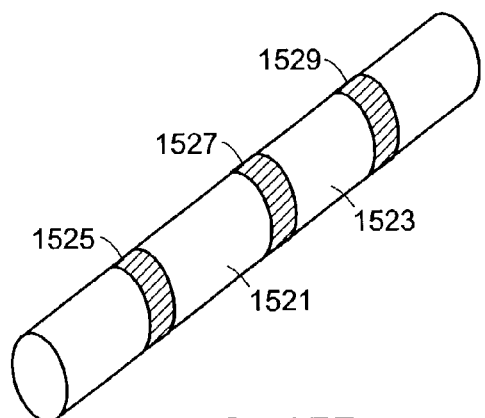
FIG. 15b is a side view of a device of the present invention having axially segmented electrodes.

In some embodiments, the plurality of active electrodes are axially segmented along the axis of the shaft. Now referring to FIG. 15b, there is provided a side view of a preferred active electrode configuration of the present invention. In this configuration, there is provided axially alternating active electrodes 1521, 1523 between insulating elements 1525, 1527 and 1529. These elements could be activated by connecting 1521 to active and 1523 to return, of the generator means. If 1521 was of a larger surface area than 1523, more heating will occur around the small surface area electrode. In a monopolar setup, the electrodes could be operated separately whether by multiplexing each in time or by applying the same or different voltages to each electrode.

In one configuration, each individual electrode terminal in the electrode array is electrically insulated from all other electrode terminals in the array within the shaft, and is connected to a power source that is isolated from each of the other electrode terminals in the array or to circuitry that limits or interrupts current flow to the electrode terminal when a low resistivity material (e.g., blood) causes a lower impedance path between the return electrode and the individual electrode terminal. The isolated power sources for each individual electrode terminal may constitute separate power supply circuits having internal impedance characteristics that act to limit the supply of power to the associated electrode terminal when a low impedance return path is encountered. By way of example, the isolated power source may be a user-selectable constant current source. In this embodiment, lower impedance paths will automatically result in lower resistive heating levels since the heating is proportional to the square of the operating current times the impedance. Alternatively, a single power source may be connected to each of the electrode terminals through independently actuatable switches, or by independent current limiting elements, such as inductors, capacitors, resistors and/or combinations thereof. The current limiting elements may be provided in the shaft, connectors, cable, controller or along the conductive path from the controller to the distal tip of the device. Alternatively, resistance and/or capacitance may be provided on the surface of the active electrode terminal(s) by providing an oxide layer that forms selected electrode terminals (e.g., titanium or a resistive coating on the surface of metal, such as platinum).

In a preferred aspect of the invention, the active electrode comprises an electrode array having a plurality of electrically isolated electrode terminals disposed over a contact surface (which may be a planar or non-planar surface, and which may be located at the distal tip of the device or over a lateral surface of the shaft, or over both the tip and lateral surface(s)). The electrode array will include at least two and preferably more electrode terminals, and may further comprise a temperature sensor. In a preferred aspect, each electrode terminal will be connected to the proximal connector by an electrically isolated conductor disposed within the shaft. The conductors permit independent electrical coupling of the electrode terminals to a high frequency power supply and control system with optional temperature monitoring of the operation of the probe. The control system preferably incorporates active and/or passive current limiting structures, which are designed to limit current flow when the associated electrode terminal is in contact with a low resistance return path back to the return electrode.

The use of such electrode arrays in electrosurgical procedures is particularly advantageous as it has been found to limit the depth of tissue necrosis without substantially reducing power delivery. Since the shaft is hollow, a conductive fluid could be added through the annulus of the shaft and flow into the bone structure for the purposes of lowering the electrical impedance and filling the spaces in the cancellous bone to make the target tissue a better conductor.

Another characteristic of conventional thermal-therapy electrode devices is the dimensionally-fixed nature of the electrode. Because of this fixed nature, the electrode can not be moved relative to the shaft, and so can not provide spatially-changing therapy unless the shaft is moved as well. Because it is often problematic to move the shaft, the fixed nature of the electrode limits the extent of thermal therapy.

Figure 16:
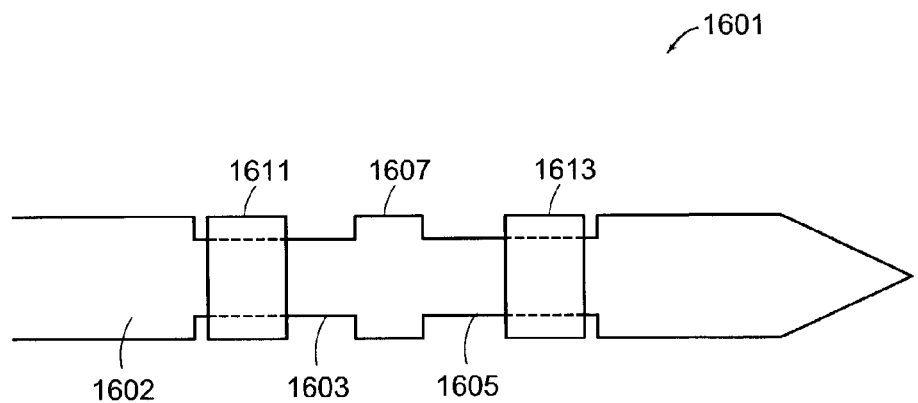
FIG. 16 is a side view of a device of the present invention having slidable electrodes.

Now referring to FIG. 16, in one aspect of the present invention, there is provided a thermal therapy device 1601 having a sliding electrode. In one embodiment, the shaft 1602 comprises first 1603 and second 1605 elongate portions having a reduced diameter. These reduced diameter portions are separated by an intermediate shaft portion 1607 of the shaft having a larger diameter. First 1611 and second 1613 annular electrodes has bores dimensioned so as to be slidable within those reduced diameter sections so that when the electrodes are placed upon the reduced diameter sections, slidable movement within those reduced diameter sections is obtained. Because the electrode is slidable, the electrodes may be moved to different axial locations, thereby providing the clinician with the ability to easily change the heating pattern at any selected axial location.

In some embodiments, each of the sliding electrodes is moved towards intermediate portion 1607. This results in a smaller gap between the electrodes and consequently a more compact heating pattern.

In some embodiments, each of the sliding electrodes is moved away from intermediate portion 1607. This results in a larger gap between the electrodes and consequently a more elongated heating pattern. If the gap is sufficiently large, then the heating pattern may form two essentially separate zones adjacent to the electrodes.

In some embodiments, each of the sliding electrodes is moved in the same direction (i.e., distally). This results in a more distal heating pattern.

Therefore, in accordance with the present invention, there is provided a thermal therapy device comprising:
a) a shaft having:
 i) an first outer surface having first and second portions having a first diameter, and
 ii) a first reduced diameter outer surface located between the first and second portions having the first diameter,
b) a first annular electrode disposed on the reduced diameter outer surface of the shaft and dimensioned so as to be slidable upon the reduced diameter outer surface, the electrode being in electrical connection with a power supply.

Also in accordance with the present invention, there is provided a thermal therapy device comprising:
a) a shaft having:
 i) an first outer surface having first, second and third portions having a first diameter, and
 ii) first and second reduced diameter outer surface portions, the first being located between the first and second portions having the first diameter, and the second being located between the second and third portions having the first diameter,
b) a first and second annular electrodes disposed on the reduced diameter outer surface of the shaft and dimensioned so as to be slidable upon the respective first and second reduced diameter outer surfaces, each electrode being in electrical connection with a power supply so as to form and active and return electrode.

It should be clearly understood that the invention is not limited to electrically isolated electrode terminals, or even to a plurality of electrode terminals. For example, an array of active electrode terminals may be connected to a single lead that extends through the shaft to a power source of high frequency current. Alternatively, the device may incorporate a single electrode extending directly through the shaft or connected to a single lead that extends to the power source. The active electrode(s) may have a shape selected from the group consisting of a ball shape, a twizzle shapes, a spring shape, a twisted metal shape, a cone shape, an annular shape and a solid tube shape. Alternatively, the electrode(s) may comprise a plurality of filaments, rigid or flexible brush electrode(s), side-effect brush electrode(s) on a lateral surface of the shaft, coiled electrode(s) or the like.

The current applied between the return electrode(s) and the electrode terminal(s) is preferably a high or radio frequency current, typically between about 50 kHz and 20 MHz, usually being between about 100 kHz and 2.5 MHz, preferably being between about 400 kHz and 1000 kHz, often less than 600 kHz, and often between about 500 kHz and 600 kHz. The RMS (root mean square) voltage applied will usually be in the range from about 5 volts to 1000 volts, preferably being in the range from about 10 volts to 200 volts, often between about 20 to 100 volts depending on the electrode terminal size, the operating frequency and the operation mode of the particular procedure. Lower peak-to-peak voltages are preferred for thermal heating of tissue, and will typically be in the range from 100 to 1500, preferably 45 to 1000 and more preferably 45 to 80 volts rms. As discussed above, the voltage is usually delivered continuously with a sufficiently high frequency RF current (e.g., on the order of 50 kHz to 20 MHz) as compared with e.g., lasers that produce small depths of necrosis and are generally pulsed about 10 to 20 Hz. In addition, the sine wave duty cycle (i.e., cumulative time in any one-second interval that energy is applied) is preferably on the order of about 100% for the present invention, as compared with pulsed lasers which typically have a duty cycle of about 0.0001%.

The power source allows the user to select the power level according to the specific requirements of a particular procedure. The preferred power source of the present invention delivers a high frequency current selectable to generate average power levels ranging from several milliwatts to tens of watts per electrode, depending on the volume of target tissue being heated, and/or the maximum allowed temperature selected for the device tip.

The power source may be current limited or otherwise controlled so that undesired heating of the target tissue or surrounding (non-target) tissue does not occur. In one embodiment of the present invention, current limiting inductors are placed in series with each independent electrode terminal, where the inductance of the inductor is in the range of 10 uH to 50,000 uH, depending on the electrical properties of the target tissue, the desired tissue heating rate and the operating frequency. Alternatively, capacitor-inductor (LC) circuit structures may be employed, as described previously in U.S. Pat. No. 5,697,909. Additionally, current limiting resistors may be selected. Preferably, microprocessors are employed to monitor the measured current and control the output to limit the current.

The area of the tissue treatment surface can vary widely, and the tissue treatment surface can assume a variety of geometries, with particular areas and geometries being selected for specific applications. The geometries can be planar, concave, convex, hemispherical, conical, linear "in-line" array or virtually any other regular or irregular shape. Most commonly, at least one of the active electrode(s) or electrode terminal(s) will be formed at the distal tip of the device, and is frequently planar, disk-shaped, or hemispherical. Alternatively or additionally, the active electrode(s) may be formed on lateral surfaces of the electrosurgical instrument shaft (e.g., in the manner of a spatula), facilitating access to certain body structures in endoscopic procedures.

The devices of the present invention may be suitably used for insertion into any hard or soft tissue in the human body, but are most advantageously used in hard tissue. In some embodiments, the hard tissue is bone. In other embodiments, the hard tissue is cartilage. In preferred embodiments when bone is selected as the tissue of choice, the bone is a vertebral body. Preferably, the present invention is adapted to puncture the hard cortical shell of the bone and penetrate at least a portion of the underlying cancellous bone. In some embodiments, the probe advances into the bone to a distance of at least ⅓ of the cross-section of the bone defined by the advance of the probe.

In some embodiments, there is provided a preferred procedure comprising a first step of penetrating the hard cortical bone with a sharp tipped biopsy needle housed in a cannula, and a second step of delivering a device of the present invention having a radiused or bullet nose through the cannula through the location of pierced bone.

In some embodiments, the present invention is practiced in vertebral bodies substantially free of tumors. In others, the present invention is practiced in vertebral bodies having tumors.

In some embodiments, the target region of the basivertebal nerve (BVN) is located within the cancellous portion of the bone (i.e., to the interior of the outer cortical bone region), and proximal to the junction of the BVN having a plurality of branches. Treatment in this region is advantageous because only a single portion of the BVN need be effectively treated to denervate the entire system. In contrast, treatment of the BVN in locations more downstream than the junction require the denervation of each branch.

Figure 17:
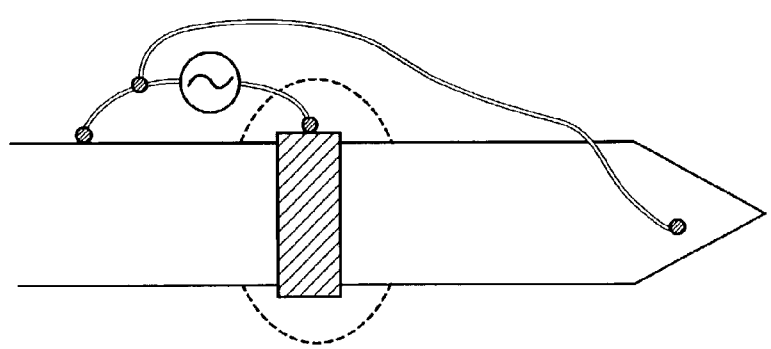
FIG. 17 is a side view of a device of the present invention in which both the tip and shaft of the device are return electrodes.

In another embodiment, as in FIG. 17, the electrical connections between the device and the power supply can be configured so as to cause each of the tip and the shaft to become return electrodes that sandwich an active electrode.

Figure 18A:
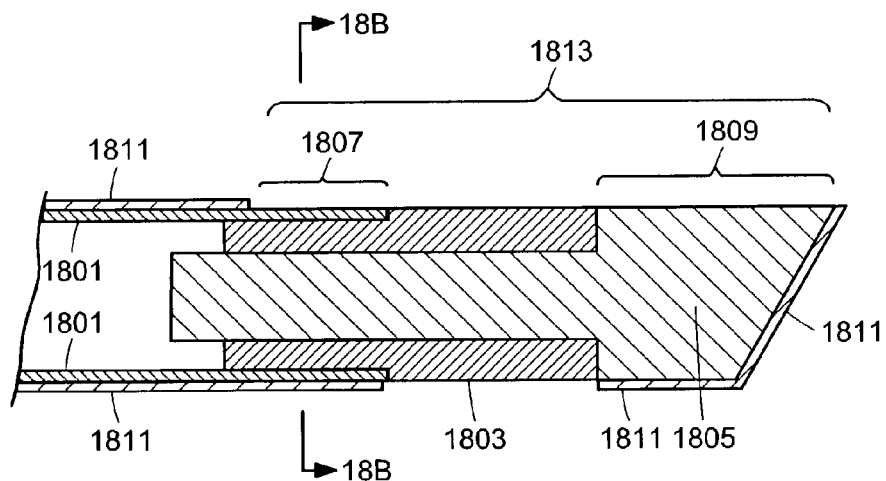
FIGS. 18a and 18b present axial and transverse cross-sectional views of an embodiment of the present invention in which the electrode surfaces are configured to allow current to flow out of only one side of the device.
Figure 18B:
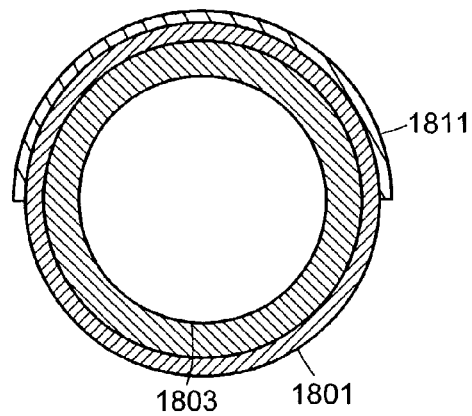

In some embodiments of the present invention, the insulation and/or electrode geometries are selected to provide a more directional flow of current out of the device. In some embodiments, the electrode portions and insulating portions of the device are configured so that current flows through a hemi-cylindrical portion of a transverse cross-section of the device. For example, in some embodiments, as shown in FIGS. 18a and 18b, there is provided a device comprising a shaft 1801, a spacer 1803, and a tip 1805. The electrode portions 1807, 1809 and insulation portions 1811 of the device are configured so that current flows only across a first side 1813 of the device.

Although the embodiment shown in FIGS. 18a and 18b describes an active electrode surface of about 180°, other variations in the arc circumscribed by the active electrode surface are also contemplated (such as about 90°, about 270°).

In other embodiments, the active electrode surface area may change along the longitudinal axis, thereby varying the heating profile. For example, the active electrode surface may taper from a proximal 180° arc to a distal 90° arc.

In some embodiments, there is provided a device having a telescoping deployment of the electrodes. Now referring to FIGS. 19a and 19b, there is provided a device of the present invention having insulating portions 1901 and electrodes 1903, wherein the distal tip 1905 and the electrodes 1903 are mounted on an inner shaft 1907 contained within a hollow outer hollow shaft 1909 in a concentric telescoping manner, such that the distal tip and the electrodes of the inner shaft are deployable from the hollow outer shaft. FIG. 19a presents the device in an undeployed configuration, while FIG. 19b presents the device in a deployed configuration. In this embodiment, an electrode 1903 is located on the distal tip 1905 of the inner shaft.

In some embodiments, the hollow outer shaft contains one or more electrodes 1904 located on or near the distal end 1911 of the hollow outer shaft.

In some embodiments, deployment of the electrodes is carried out by a simple sliding motion.

In others, the inner portion of the outer shaft and the outer portion of the inner shaft comprise complementary thread-forms, so that the relative rotation of one of the shafts causes linear distal displacement of the inner shaft. The mechanical advantage provided by this embodiment provides the clinician with an increased force and increased precision.

In another embodiment, the inner portion of the outer shaft and the outer portion of the inner shaft form a complementary pin-and-helical groove structure. This embodiment allows for a more rapid deployment of the electrodes to a fixed distal position.

Deployment mechanisms for these embodiments are well known in the art and are preferably located in part upon the proximal portion of a handle of the device.

This telescoping embodiment advantageously provides the surgeon with an ability to adjust the location of an electrodes without moving the entire probe. That is, the surgeon may treat a first location, adjust the location of the electrode by telescoping, and then treat a second location.

Therefore, in accordance with the present invention, there is provided a thermal therapy device comprising:
 a) an outer shaft 1909 having i) a hollow bore 1921 defining an inner surface 1923 and an distal opening 1925, and ii) a first electrode 1904;
 b) an inner shaft 1907 having i) an outer surface 1927 dimensioned so as to be axially movable within the bore of the outer shaft and across the distal opening of the outer shaft, and ii) a second electrode 1903,
 wherein the first and second electrodes are in electrical connection with a power supply to provide a voltage therebetween.

EXAMPLE I

This prophetic example describes a preferred dual probe embodiment of the present invention.

First, after induction of an appropriate amount of a local anesthesia, the human patient is placed in a prone position on the table. The C-arm of an X-ray apparatus is positioned so that the X-rays are perpendicular to the axis of the spine. This positioning provides a lateral view of the vertebral body, thereby allowing the surgeon to view the access of the apparatus into the vertebral body.

Next, the device of the present invention is inserted into the skin at a lateral location so that its distal tip passes posterior to the dorsal nerves located outside the vertebral body.

Next, the device is advanced interiorly into the vertebral body so that the distal tip bores through the skin, into and through the cortical shell of the vertebral body. The device is advanced until the tip reaches the anterior-posterior midline of the vertebral body.

Next, the power supply is activated to provide a voltage between the active and return electrodes. The amount of voltage across the electrodes is sufficient to produce an electric current between the active and return electrodes. This current provides resistive heating of the tissue disposed between the electrodes in an amount sufficient to raise the temperature of the local portion of the basivertebral nerve (BVN) to at least 45° C., thereby denervating the BVN.

What is claimed is:
1. An electrosurgical device, comprising:
 an elongate shaft having a proximal end and a distal end, at least a portion of said elongate shaft comprising an electrically conductive material;
 an intermediate spacer having a proximal end and a distal end, said intermediate spacer comprising an electrically insulating material,
 wherein said proximal end of said intermediate spacer is mechanically connected to said distal end of said elongate shaft; and a sharp tip comprising an electrically conductive material having a proximal end and a distal end, wherein said proximal end of said tip is mechanically connected to said distal end of said intermediate spacer, wherein said distal end of said sharp tip is configured to pierce cortical bone of a vertebral body, wherein said elongate shaft is electrically connected to a power supply via a first lead, wherein said sharp tip is connected to said power supply via a second lead, wherein said elongate shaft and said tip form a bipolar heating device, and wherein said bipolar heating device is configured to denervate an intraosseous nerve within a cancellous bone region of a vertebral body by transmission of radiofrequency energy to heat at least a portion of the cancellous bone region.

2. The device of claim 1 wherein said elongate shaft is hollow, wherein said intermediate spacer is hollow, and wherein said second lead runs through said elongate shaft and said intermediate spacer.

3. The device of claim 1, wherein at least a portion of said elongate shaft comprises an outer insulating sleeve to electrically isolate the shaft from adjacent tissue.

4. The device of claim 3, wherein the sleeve has a length that is between 50% and 95% of the length of the shaft.

5. The device of claim 1, wherein the elongate shaft is flexible.

6. The device of claim 1, wherein the elongate shaft comprises a shape memory alloy.

7. The device of claim 1, wherein said proximal end of said intermediate spacer extends inside said distal end of said elongate shaft, and wherein said proximal end of said sharp tip extends inside said proximal end of said intermediate spacer.

8. The device of claim 7, wherein the proximal end of the sharp tip is nested through the intermediate spacer and into the distal end of the shaft, thereby imparting electrical isolation and greater strength to the device.

* * * * *